United States Patent
Ye et al.

(10) Patent No.: US 10,000,593 B2
(45) Date of Patent: Jun. 19, 2018

(54) SUPPORTED SALAN CATALYSTS

(71) Applicant: ExxonMobil Chemical Patents Inc., Baytown, TX (US)

(72) Inventors: Xuan Ye, Houston, TX (US); Crisita Carmen H. Atienza, Houston, TX (US); Matthew W. Holtcamp, Huffman, TX (US); David F. Sanders, Houston, TX (US); Gregory S. Day, College Station, TX (US); Michelle E. Titone, Houston, TX (US); David A. Cano, Houston, TX (US); Matthew S. Bedoya, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

(21) Appl. No.: 15/242,198

(22) Filed: Aug. 19, 2016

(65) Prior Publication Data

US 2017/0096508 A1    Apr. 6, 2017

Related U.S. Application Data

(60) Provisional application No. 62/236,691, filed on Oct. 2, 2015.

(51) Int. Cl.
| | |
|---|---|
| C08F 4/64 | (2006.01) |
| C08F 4/76 | (2006.01) |
| C08F 210/16 | (2006.01) |
| C07F 7/00 | (2006.01) |
| C08F 4/60 | (2006.01) |

(52) U.S. Cl.
CPC .............. C08F 210/16 (2013.01); C07F 7/00 (2013.01); C08F 4/60189 (2013.01); C08F 4/64 (2013.01); C08F 4/64189 (2013.01)

(58) Field of Classification Search
CPC .................... C08F 4/60189; C08F 4/64189
See application file for complete search history.

(56) References Cited

U.S. PATENT DOCUMENTS

| | | |
|---|---|---|
| 5,308,811 A | 5/1994 | Suga et al. |
| 5,830,820 A | 11/1998 | Yano et al. |
| 5,928,982 A | 7/1999 | Suga et al. |
| 5,973,084 A | 10/1999 | Suga et al. |
| 6,103,657 A | 8/2000 | Murray |
| 6,274,684 B1 | 8/2001 | Loveday et al. |
| 6,333,423 B1 | 12/2001 | Kol et al. |
| 6,368,999 B1 | 4/2002 | Speca |
| 6,399,535 B1 | 6/2002 | Shih et al. |
| 6,531,552 B2 | 3/2003 | Nakano et al. |
| 6,559,090 B1 | 5/2003 | Shih et al. |
| 6,596,827 B2 | 7/2003 | Kol et al. |
| 6,664,348 B2 | 12/2003 | Speca |
| 6,734,131 B2 | 5/2004 | Shih et al. |
| 6,844,389 B2 | 1/2005 | Mehta et al. |
| 6,900,321 B2 | 5/2005 | Boussie et al. |
| 6,943,224 B2 | 9/2005 | Shih |
| 7,183,348 B2 | 2/2007 | Reinking et al. |
| 7,220,695 B2 | 5/2007 | Casty et al. |
| 7,355,058 B2 | 4/2008 | Luo et al. |
| 7,754,840 B2 | 7/2010 | Loveday et al. |
| 7,973,116 B2 | 7/2011 | Hagadorn et al. |
| 8,071,701 B2 | 12/2011 | Klosin et al. |
| 8,080,613 B2 | 12/2011 | Moad et al. |
| 8,110,518 B2 | 2/2012 | Marin et al. |
| 8,575,284 B2 | 11/2013 | Luo et al. |
| 8,791,217 B2 | 7/2014 | Hlavinka et al. |
| 8,907,032 B2 | 12/2014 | Kol et al. |
| 8,937,137 B2 | 1/2015 | Holtcamp et al. |
| 8,952,114 B2 | 2/2015 | Giesbrecht et al. |
| 8,957,171 B2 | 2/2015 | Giesbrecht et al. |
| 8,957,172 B2 | 2/2015 | Giesbrecht et al. |
| 9,079,991 B2 | 7/2015 | Ker et al. |
| 9,120,879 B2 | 9/2015 | Giesbrecht et al. |
| 9,150,676 B2 | 10/2015 | Kol et al. |
| 9,193,813 B2 | 11/2015 | Kol et al. |
| 9,200,099 B2 | 12/2015 | Kol et al. |
| 9,200,100 B2 | 12/2015 | Kol et al. |
| 9,290,589 B2 | 3/2016 | Evans et al. |
| 2002/0019503 A1 | 2/2002 | Kol et al. |
| 2002/0123582 A1 | 9/2002 | Speca |
| 2002/0142912 A1 | 10/2002 | Boussie et al. |
| 2003/0027950 A1 | 2/2003 | Uchino et al. |
| 2003/0096698 A1 | 5/2003 | Shih et al. |
| 2005/0148743 A1 | 7/2005 | Casty et al. |
| 2006/0293470 A1 | 12/2006 | Cao et al. |
| 2010/0227990 A1 | 9/2010 | Kuhlman et al. |
| 2012/0027017 A1 | 2/2012 | Rai et al. |

(Continued)

FOREIGN PATENT DOCUMENTS

| | | |
|---|---|---|
| EP | 511665 A1 | 11/1992 |
| EP | 1 160 261 A1 | 12/2001 |

(Continued)

OTHER PUBLICATIONS

U.S. Appl. No. 62/168,302, filed May 29, 2015, Holtcamp et al.
U.S. Appl. No. 62/222,935, filed Sep. 24, 2015, Holtcamp et al.
U.S. Appl. No. 62/236,712, filed Oct. 2, 2015, Atienza et al.
U.S. Appl. No. 62/236,720, filed Oct. 2, 2015, Atienza et al.
Bucheli et al., "Spherical Clay Conglomerates: A Novel Stationary Phase for Solid-Phase Extraction and 'Reversed-Phase' Liquid Chromatography," Analytical Chemistry, vol. 71(11), Jun. 1, 1999, pp. 2171-2178.
Busico et al., "Block Copolymers of Highly Isotactic Polypropylene via Controlled Ziegler-Natta Polymerization," Macromolecules, 2004, vol. 37, pp. 8201-8203.
Cipullo et al., "Improving the Behavior of Bis(phenoxyamine) Group 4 Metal Catalysts for Controlled Alkene Polymerization," Macromolecules, 2009, vol. 42, pp. 3869-3872.

(Continued)

*Primary Examiner* — Rip A Lee

(57) ABSTRACT

A catalyst system including the reaction product of a fluorided support, an activator, and at least a first transition metal catalyst compound; methods of making such catalyst systems, polymerization processes using such catalyst systems, and polymers made therefrom.

47 Claims, No Drawings

(56) References Cited

U.S. PATENT DOCUMENTS

| | | | |
|---|---|---|---|
| 2013/0035463 A1 | 2/2013 | Cann et al. | |
| 2013/0131294 A1 | 5/2013 | Hagadorn et al. | |
| 2013/0172498 A1 | 7/2013 | Hlavinka et al. | |
| 2014/0031504 A1 | 1/2014 | Jacobsen et al. | |
| 2014/0039137 A1 | 2/2014 | Giesbrecht et al. | |
| 2014/0039138 A1 | 2/2014 | Giesbrecht | |
| 2014/0039139 A1 | 2/2014 | Giesbrecht et al. | |
| 2014/0121341 A1 | 5/2014 | Holtcamp et al. | |
| 2014/0128557 A1* | 5/2014 | Giesbrecht | C08F 4/64189 526/127 |
| 2014/0221587 A1 | 8/2014 | Hagadorn et al. | |
| 2014/0275454 A1 | 9/2014 | Holtcamp et al. | |
| 2015/0141601 A1 | 5/2015 | Hagadorn et al. | |
| 2015/0329652 A1 | 11/2015 | Hlavinka | |
| 2017/0088641 A1 | 3/2017 | Holtcamp et al. | |
| 2017/0096506 A1 | 4/2017 | Ye et al. | |
| 2017/0096507 A1 | 4/2017 | Atienza et al. | |
| 2017/0096509 A1 | 4/2017 | Atienza et al. | |
| 2017/0096510 A1 | 4/2017 | Ye et al. | |
| 2017/0096511 A1 | 4/2017 | Atienza et al. | |

FOREIGN PATENT DOCUMENTS

| | | |
|---|---|---|
| EP | 0 849 292 B1 | 8/2002 |
| JP | 1995033814 A | 2/1995 |
| JP | 2011089019 A | 5/2011 |
| JP | 2013124302 A | 6/2013 |
| WO | 97/48743 A1 | 12/1997 |
| WO | 01/42320 A1 | 6/2001 |
| WO | 02/088198 A1 | 11/2002 |
| WO | 2004/106390 A2 | 12/2004 |
| WO | 2005/075575 | 8/2005 |
| WO | 2006/036748 A2 | 4/2006 |
| WO | 2007/018804 A1 | 2/2007 |
| WO | 2012/033670 A1 | 3/2012 |
| WO | 2012/098521 A1 | 7/2012 |
| WO | 2012/134614 A1 | 10/2012 |
| WO | 2012/134615 A1 | 10/2012 |
| WO | 2012/158260 A1 | 11/2012 |
| WO | 2013/028283 | 2/2013 |
| WO | 2013/040276 A1 | 3/2013 |
| WO | 2014/143202 A1 | 9/2014 |
| WO | 2014/149361 A1 | 9/2014 |
| WO | 2015/088819 | 6/2015 |
| WO | 2017/039994 | 3/2017 |
| WO | 2017/039995 | 3/2017 |

OTHER PUBLICATIONS

Meurs et al., "Polyethylene Chain Growth on Zinc Catalyzed by Olefin Polymerization Catalysts: A Comparative Investigation of Highly Active Catalyst Systems across the Transition Series ," J. Am. Chem. Soc., 2005, vol. 127, pp. 9913-9923.

Reybuck et al., "Amine Bis(phenolate) Zirconium Complexes: Influence of Ligand Structure and Cocatalyst on Copolymerization Behaivor," Macromolecules, 2005, vol. 38, pp. 2552-2558.

Su et al., "Oxo-Bridged Bimetallic Group 4 Complexes Bearing Amine-Bis(benzotriazole phenolate) Derivatives as Bifunctional Catalysts for Ring-Opening Polymerization of Lactide and Copolymerization of Carbon Dioxide with Cyclohexene Oxide," Organometallics, 2014, vol. 33, pp. 7091-7100.

Valente et al., "Coordinative Chain Transfer Polymerization," Chemical Reviews, 2013, vol. 113, pp. 3836-3857.

U.S. Appl. No. 15/051,421, filed Feb. 23, 2016, Atienza et al.
U.S. Appl. No. 61/779,435, filed Mar. 13, 2013, Holtcamp et al.
U.S. Appl. No. 62/149,799, filed Apr. 20, 2015, Ye et al.
U.S. Appl. No. 61/149,814, filed Apr. 20, 2015, Ye et al.
U.S. Appl. No. 62/236,697, filed Oct. 2, 2015, Ye et al.
U.S. Appl. No. 62/236,701, filed Oct. 2, 2015, Atienza et al.
U.S. Appl. No. 62/236,727, filed Oct. 2, 2015, Ye et al.

Barroso, et al., "Chiral Diamine Bis(phenolate) $Ti^{IV}$ and $ZR^{IV}$ Complexes—Synthesis, Structures and Reactivity," Eur. J. Inorg. Chem, 2011, pp. 4277-4290.

Gibson et al., "*Advances in Non-Metallocene Olefin Polymerization Catalysis*," Chem. Rev., 2003, vol. 103, pp. 283-315.

Groysman et al., "*Diverse Structure-Activity Trends in Amine Bis(phenolate) Titanium Polymerization Catalysts*," Organometallics 2004, vol. 23, pp. 5291-5299.

Groysman et al., "*From THF to Furan: Activity Tuning and Mechanistic Insight via Sidearm Donor Replacement in Group IV Amine Bis(phenolate) Polymerization Catalysts*," Organometallics, 2003, vol. 22, pp. 3013-3015.

Tshuva et al., "*[ONXO]—Type Amine Bis(phenolate) Zirconium and Hafnium Complexes as Extremely Active 1-Hexene Polymerization Catalysts*," Organometallics, 2002, vol. 21, pp. 662-670.

U.S. Appl. No. 62/332,940, filed May 6, 2016 Holtcamp et al.
PCT/US2017/055131 filed Oct. 4, 2017 Hule et al.
U.S. Appl. No. 62/410,173, filed Oct. 19, 2016 Hule et al.

\* cited by examiner

SUPPORTED SALAN CATALYSTS

CROSS REFERENCE TO RELATED APPLICATIONS

This invention claims priority to and the benefit of U.S. Ser. No. 62/236,691, filed Oct. 2, 2015, which is incorporated by reference in its entirety.

FIELD OF THE INVENTION

This invention relates to supported Salan catalysts, processes utilizing such catalysts, and polymers produced thereby.

BACKGROUND OF THE INVENTION

Supported olefin polymerization catalysts are of great use in industry. Hence, there is interest in finding new supported catalyst systems that increase the commercial usefulness of the catalyst and allow the production of polymers having improved properties.

There is a need in the art for new and improved supported catalysts and catalyst systems to obtain new and improved polyolefins, polymerization processes, and the like. Accordingly, there is a need in the art for new and improved supported catalyst systems for the polymerization of olefins, in order to achieve specific polymer properties with improved catalyst operability.

SUMMARY OF THE INVENTION

The instant disclosure is directed to supported catalyst compounds, supported activators, and catalyst systems comprising such compounds, processes for the preparation of the catalyst compounds and systems, and processes for the polymerization of olefins using such supported catalyst compounds and systems.

Thus, in one aspect, some embodiments of the invention relate to catalyst systems comprising the reaction product of fluorided support (such as fluorided silica) that preferably has not been calcined at a temperature of 400° C. or more, an activator and a catalyst compound represented by Formula I:

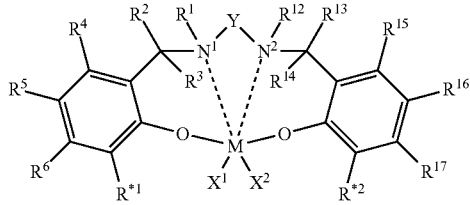

Formula I wherein:
each solid line represents a covalent bond and each dashed line represents a coordinative link;
wherein M is a Group 3, 4, 5, or 6 transition metal;
$N^1$ and $N^2$ are nitrogen;
O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure, provided however when M is trivalent $X^2$ is not present;
each $R^1$, $R^2$, $R^3$, $R^4$, $R^5$, $R^6$, $R^{12}$, $R^{13}$, $R^{14}$, $R^{15}$, $R^{16}$, and $R^{17}$ is independently, hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), two or more of $R^1$, $R^2$, $R^3$, $R^4$, $R^5$, $R^6$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof;
wherein $R^{*1}$ and $R^{*2}$ independently comprise a bulky functional group, an electron withdrawing group, or a combination thereof; and
Y is a divalent $C_1$ to $C_{20}$ hydrocarbyl radical.

In another aspect, some embodiments of the invention relate to processes comprising: contacting one or more olefins with a catalyst system described herein at a temperature, a pressure, and for a period of time sufficient to produce a polyolefin.

In still another aspect, some embodiments of the invention relate to polyolefins comprising ethylene, wherein the polyolefin is produced by a process comprising: contacting ethylene and, optionally one or more comonomers with a catalyst system described herein at a temperature, a pressure, and for a period of time sufficient to produce a polyolefin.

DETAILED DESCRIPTION OF THE INVENTION

The specification describes supported catalyst systems that include the reaction product of a fluorided silica, at least one transition metal catalyst compound, and an activator. The term "transition metal catalyst compound" is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The catalyst compounds are generally subjected to activation to perform their polymerization or oligomerization function using an activator, which is believed to create a cation as a result of the removal of an anionic group, often referred to as a leaving group, from the transition metal.

In the structures depicted throughout this specification and the claims, a solid line indicates a bond, and a dashed line represents a coordinative link between the atoms.

As used herein, the numbering scheme for the Periodic Table groups is the new notation as set out in Chemical and Engineering News, 63(5), 27, (1985).

The terms "hydrocarbyl radical," "hydrocarbyl" and "hydrocarbyl group" are used interchangeably throughout this document unless otherwise specified. For purposes of this disclosure, a hydrocarbyl radical is defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic and aromatic or non-aromatic.

For the purposes of this invention and the claims thereto, the new numbering scheme for the Periodic Table Groups is used as in Chem. Eng. News, 1985, 63, 27. Therefore, a "Group 4 metal" is an element from Group 4 of the Periodic Table.

The terms "hydrocarbyl radical," "hydrocarbyl," and "hydrocarbyl group" are used interchangeably throughout this document unless otherwise specified. For purposes of this disclosure, hydrocarbyl radicals are defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic where appropriate (aromatic or non-aromatic) and includes hydrocarbyl radicals substituted with other hydrocarbyl radicals. In addition, two or more such hydrocarbyl radicals may together form a fused ring system, including partially or fully hydrogenated fused ring systems, which may include heterocyclic radicals.

The term "substituted" means that a hydrogen atom or a carbon atom of a hydrocarbyl radical has been replaced by a heteroatom or a heteroatom-containing group. For purposes herein, a heteroatom is defined as any atom other than carbon and hydrogen. For example, methyl cyclopentadiene (Cp) is a Cp group wherein one hydrogen has been replaced with a methyl radical, which may also be referred to as a methyl functional group; ethyl alcohol is an ethyl group, wherein one of the H atoms has been replaced with the heteroatom-containing group —OH, and pyridine is considered a substituted phenyl group wherein a carbon of the benzene ring has been replaced with a nitrogen atom.

Exemplary hydrocarbyl radicals include methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl.

The term "aryl," "aryl radical," and/or "aryl group" refers to aromatic cyclic structures. An aralkyl group is defined to be an aryl group having at least one H atom replaced by an alkyl group, such as a $C_1$ to $C_{40}$ alkyl. Examples of aryl and aralkyl radicals include, but are not limited to: acenaphthenyl, acenaphthylenyl, acridinyl, anthracenyl, benzanthracenyls, benzimidazolyl, benzisoxazolyl, benzofluoranthenyls, benzofuranyl, benzoperylenyls, benzopyrenyls, benzothiazolyl, benzothiophenyls, benzoxazolyl, benzyl, carbazolyl, carbolinyl, chrysenyl, cinnolinyl, coronenyl, cyclohexyl, cyclohexenyl, methylcyclohexyl, dibenzoanthracenyls, fluoranthenyl, fluorenyl, furanyl, imidazolyl, indazolyl, indenopyrenyls, indolyl, indolinyl, isobenzofuranyl, isoindolyl, isoquinolinyl, isoxazolyl, methyl benzyl, methylphenyl, naphthyl, oxazolyl, phenanthrenyl, phenyl, pentamethylphenyl, trimethylphenyl, e.g., 2,4,6-trimethylphenyl, purinyl, pyrazinyl, pyrazolyl, pyrenyl, pyridazinyl, pyridinyl, pyrimidinyl, pyrrolyl, quinazolinyl, quinolonyl, quinoxalinyl, thiazolyl, thiophenyl, and the like.

For purposes herein, a carbazole radical, a hydrocarbyl radical, is represented by the formula:

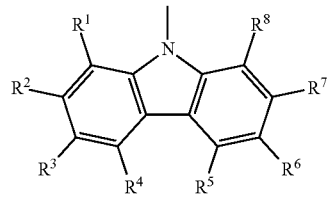

wherein:
each $R^1$ through $R^8$ is, independently, a hydrogen, a $C_1$ to $C_{40}$ hydrocarbyl radical, a substituted $C_1$ to $C_{40}$ hydrocarbyl radical (such as a functional group comprising elements from Groups 13 to 17 of the periodic table of the elements), or two or more of $R^1$ to $R^8$ may independently join together to form a $C_4$ to $C_{62}$ cyclic or polycyclic ring structure, or a combination thereof. A substituted carbazole is one where at least one of $R^1$ to $R^8$ is not H.

A fluorenyl radical, another hydrocarbyl radical, is represented by the formula:

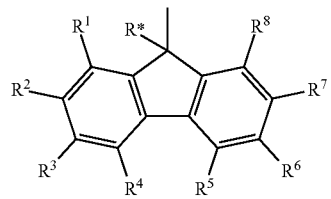

wherein:
each $R^1$ through $R^8$ is, independently, a hydrogen, a $C_1$ to $C_{40}$ hydrocarbyl radical, a substituted $C_1$ to $C_{40}$ hydrocarbyl radical (such as a functional group comprising elements from Groups 13 to 17 of the periodic table of the elements), or two or more of $R^1$ to $R^8$ may independently join together to form a $C_4$ to $C_{62}$ cyclic or polycyclic ring structure, or a combination thereof; and
$R^*$ is a hydrogen, a $C_1$ to $C_{40}$ hydrocarbyl radical, a substituted $C_1$ to $C_{40}$ hydrocarbyl radical (preferably $R^*$ is methyl, phenyl, tolyl, substituted phenyl, or substituted tolyl). A substituted fluorenyl is one where at least one of $R^*$, or $R^1$ to $R^8$ is not H.

For purposes herein, an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer.

For purposes herein, a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such as Mn of less than 25,000 g/mol, or in an embodiment less than 2,500 g/mol, or a low number of mer units, such as 75 mer units or less. An "ethylene polymer" or "ethylene copolymer" is a polymer or copolymer comprising at least 50 mol % ethylene derived units, a "propylene polymer" or "propylene copolymer" is a polymer or copolymer comprising at least 50 mole % propylene derived units, and so on.

For the purposes of this disclosure, the term "α-olefin" includes $C_2$ to $C_{22}$ olefins having a double bond at the alpha position. Non-limiting examples of α-olefins include ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane.

Non-limiting examples of cyclic olefins and diolefins include: cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

The terms "catalyst," "catalyst compound," and "transition metal compound" are defined to mean a compound capable of initiating polymerization catalysis under the appropriate conditions. In the description herein, the catalyst may be described as a catalyst precursor, a pre-catalyst compound, a transition metal compound, a Salan compound, a Salan catalyst, or a Salan catalyst compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is the combination of at least one catalyst compound, at least one activator, an optional co-activator, and a support material, where the system can polymerize monomers to polymer. For the purposes of this invention and the claims thereto, when catalyst systems are described as comprising neutral stable forms of the components, it is well understood by one of ordinary skill in the art that the ionic form of the component is the form that reacts with the monomers to produce polymers.

For purposes herein, the term "catalyst productivity" is a measure of how many grams of polymer (P) are produced using a polymerization catalyst comprising W g of catalyst (cat), over a period of time of T hours; and may be expressed by the following formula: P/(T×W) and expressed in units of gP*gcat$^{-1}$*hr$^{-1}$. Conversion is the amount of monomer that is converted to polymer product, and is reported as mol % and is calculated based on the polymer yield and the amount of monomer fed into the reactor. "Catalyst activity" is a measure of how active the catalyst is and is reported as the mass of product polymer (P) produced per mole of catalyst (cat) used (kg P/mol cat).

An "anionic ligand" is a negatively charged ligand which donates one or more pairs of electrons to a metal ion. A "neutral donor ligand" is a neutrally charged ligand which donates one or more pairs of electrons to a metal ion.

A "scavenger" is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In an embodiment a co-activator can be pre-mixed with the catalyst compound to form an alkylated catalyst compound.

As used herein, Mn is number average molecular weight, Mw is weight average molecular weight, and Mz is z average molecular weight, wt % is weight percent, vol % is volume percent, and mol % is mole percent. Molecular weight distribution (MWD) is defined to be Mw divided by Mn. Unless otherwise noted, all molecular weight units, e.g., Mw, Mn, Mz, are g/mol.

For purposes herein, a bulky functional group is defined as a functional group having a molecular size greater than or equal to an isopropyl moiety. Accordingly, for purposes herein a bulky functional group includes substituted or unsubstituted bulky aliphatic radicals having three carbons or more, bulky alicyclic radicals having three carbons or more, and/or bulky aromatic radicals having five carbons or more, each having a molecular size greater than or equal to an isopropyl moiety.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3$V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

The following abbreviations may be used throughout this specification: Me is methyl, Ph is phenyl, Et is ethyl, Pr is propyl, iPr is isopropyl, n-Pr is normal propyl, Bu is butyl, iso-butyl is isobutyl, sec-butyl is secondary butyl, tert-butyl and t-butyl are tertiary butyl, n-butyl is normal butyl, pMe is para-methyl, Bz is benzyl, THF (also referred to as thf) is tetrahydrofuran, Mes is mesityl, also known as 1,3,5-trimethylbenzene, Tol is toluene, TMS is trimethylsilyl, TIBAL is triisobutylaluminum, TNOAL is triisobutyl n-octylaluminum, MAO is methylalumoxane, MOMO is methoxymethoxy (also referred to as methoxymethyl ether), Cy is cyclohexyl, and Bn is benzyl.

For purposes herein, RT is room temperature, which is defined as 25° C. unless otherwise specified. All percentages are weight percent (wt %) unless otherwise specified.

The term "continuous" means a system that operates without interruption or cessation. For example, a continuous process to produce a polymer would be one where the reactants are continually introduced into one or more reactors and polymer product is continually withdrawn.

Catalyst Compounds

In an embodiment, the catalyst compound comprises a catalyst compound represented by Formula I:

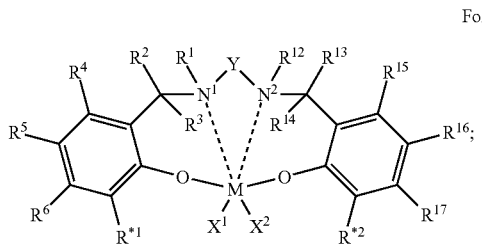

Formula I wherein:

each solid line represents a covalent bond and each dashed line represents a coordinative link; wherein M is a Group 3, 4, 5, or 6 transition metal; $N^1$ and $N^2$ are nitrogen; O is oxygen; each of $X^1$ and $X^2$ is, independently, a univalent $C_1$ to $C_{20}$ hydrocarbyl radical, a $C_1$ to $C_{20}$ substituted hydrocarbyl radical (such as a functional group comprising elements from Groups 13 to 17 of the periodic table of the elements), or $X^1$ and $X^2$ join together to form a $C_4$ to $C_{62}$ cyclic or polycyclic ring structure, provided, however, when M is trivalent $X^2$ is not present; particularly, wherein at least one of $X^1$ and/or $X^2$ is selected from $C_6$ to $C_{15}$ aryl groups, e.g., benzyl;

wherein each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$-$C_{40}$ hydrocarbyl radical, a $C_1$ to $C_{40}$ substituted hydrocarbyl radical (such as, a functional group comprising elements from Groups 13 to 17 of the periodic table of the elements), two or more of $R^1$, $R^2$, $R^3$, $R^4$, $R^5$, $R^6$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof; wherein each of $R^{*1}$ and $R^{*2}$ independently comprises a bulky functional group, an electron withdrawing group, or a combination thereof (such as, but not limited, to a substituted or unsubstituted $C_1$ to $C_{40}$ hydrocarbyl radical); and Y is a divalent $C_1$ to $C_{20}$ hydrocarbyl radical, particularly a $C_1$ to $C_5$ hydrocarbyl radical, e.g., —(CH$_2$CH$_2$)—.

Particular catalyst compositions according to Formula I will now be described.

In an embodiment, at least one of $R^{*1}$ and $R^{*2}$ independently comprises a cyclopentadienyl radical having a structure according to Formula II:

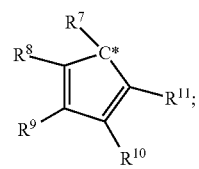

Formula II wherein:

C* indicates an attachment carbon of the radical; $R^7$ is a $C_1$ to $C_{40}$ hydrocarbyl radical, a $C_1$ to $C_{40}$ substituted hydrocarbyl radical (such as or a functional group comprising elements from Groups 13 to 17 of the periodic table of the elements); and each of $R^8$, $R^9$, $R^{10}$, $R^{11}$ is, independently, hydrogen, a $C_1$ to $C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof.

In an embodiment according to the invention, each of $R^{*1}$ and $R^{*2}$ is selected from the group consisting of substituted or unsubstituted radicals comprising any one of the following formulae:

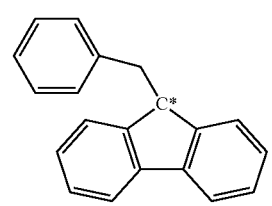

(i)

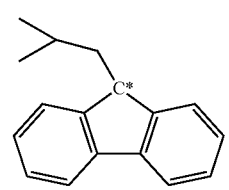

(ii)

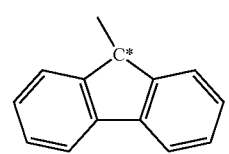

(iii)

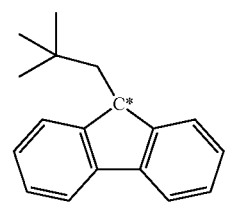

(iv)

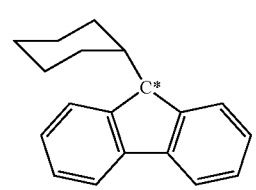

(v)

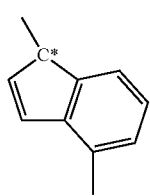 (vi)
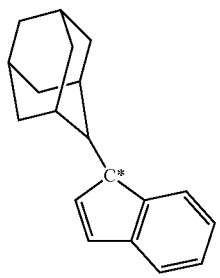 (vii)
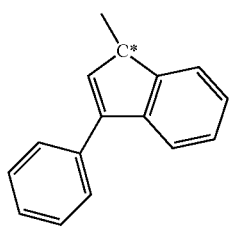 (viii)
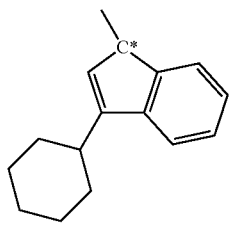 (ix)
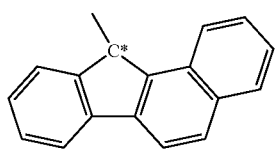 (x)
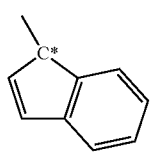 (xi)
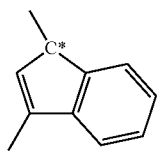 (xii)
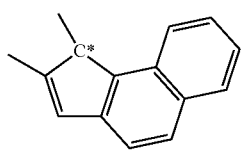 (xiii)

-continued

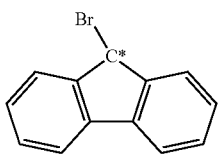
(xxiii)

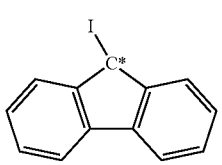
(xxiv)

wherein:

C* is the attachment carbon of the radical and each of the possible substituents of the formulae are independently, hydrogen, a $C_1$ to $C_{40}$ hydrocarbyl radical, a functional group comprising elements from Group 13 to 17 of the periodic table of the elements, or a combination thereof. In some embodiments according to the invention, each of $R^{*1}$ and $R^{*2}$ independently comprises identical radicals. In some embodiments, where $R^{*1}$ is a substituted or unsubstituted fluorenyl group, $R^{*2}$ is also a substituted or unsubstituted fluorenyl group.

In an embodiment, the catalyst compound is represented by Formula III:

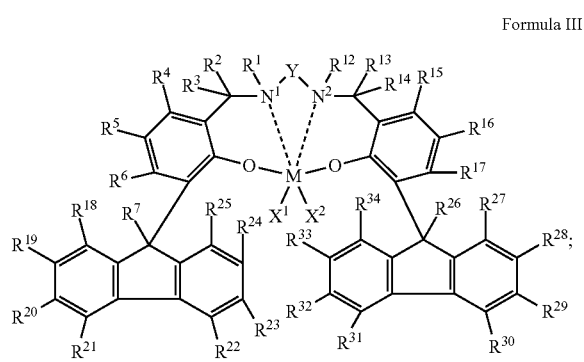

Formula III wherein:

each of $R^7$ and $R^{26}$ is, independently, a $C_1$ to $C_{40}$ hydrocarbyl radical, a $C_1$ to $C_{40}$ substituted hydrocarbyl radical (such as or a functional group comprising elements from Groups 13 to 17 of the periodic table of the elements);

wherein $R^{18}$, $R^{19}$, $R^{20}$, $R^{21}$, $R^{22}$, $R^{23}$, $R^{24}$, $R^{25}$, $R^{27}$, $R^{28}$, $R^{29}$, $R^{30}$, $R^{31}$, $R^{32}$, $R^{33}$, and $R^{34}$ is, independently, hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), and wherein two or more of $R^1$, $R^2$, $R^3$, $R^4$, $R^5$, $R^6$, $R^7$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ may independently join together to form a $C_4$ to $C_{62}$ cyclic or polycyclic ring structure, or a combination thereof, and M, O, $N^1$, $N^2$, Y, $X^1$, $X^2$, $R^1$-$R^6$, and $R^{12}$-$R^{17}$ are as defined in Formula I.

In some embodiments, at least one of $R^5$ and/or $R^{16}$ of any of the compounds according to Formulas I-III is selected from the group consisting of $C_1$ to $C_{10}$ alkyl, $C_1$ to $C_{10}$ alkoxy, and $C_6$ to $C_{15}$ aryl.

In some embodiments, $R^7$ of the catalyst compound of Formula III or Formula IV is selected from the group consisting of $C_1$ to $C_{10}$ alkyl groups, $C_1$ to $C_{10}$ alkoxy groups, $C_6$ to $C_{15}$ aryl groups, and combinations thereof. In some embodiments, each of $R^7$ and/or $R^{26}$ of catalysts, according to Formula III, is selected from the group consisting of $C_1$ to $C_{10}$ alkyl groups, $C_1$ to $C_{10}$ alkoxy groups, $C_6$ to $C_{15}$ aryl groups, and combinations thereof.

In some embodiments, each of $R^5$ and $R^{16}$ of the catalysts according to any of Formulas I-III is independently selected from the group consisting of methyl, ethyl, n-propyl, i-propyl, n-butyl, sec-butyl, i-butyl, t-butyl, methoxy, ethoxy, n-propoxy, i-propoxy, n-butoxy, sec-butoxy, i-butoxy, t-butoxy, phenyl, and $C_1$ to $C_5$ substituted phenyl groups. In some such embodiments, $R^7$, according to Formula II, is independently selected from the group consisting of ethyl, n-propyl, i-propyl, n-butyl, sec-butyl, i-butyl, t-butyl, phenyl and $C_1$ to $C_5$ substituted phenyl groups. In more particular such embodiments, each of $R^7$ and $R^{26}$, according to Formula IV, is independently selected from the group consisting of ethyl, n-propyl, i-propyl, n-butyl, sec-butyl, i-butyl, t-butyl, phenyl, and $C_1$ to $C_5$ substituted phenyl groups;

In any embodiment, the catalyst of Formulas I-III may have a formula wherein each of $R^1$, $R^2$, $R^3$, $R^4$, $R^6$, $R^{12}$, $R^{13}$, $R^{14}$, $R^{15}$, $R^{17}$, is independently selected from H and $C_1$ to $C_5$ alkyl groups. In particular such embodiments, the catalyst may follow Formula II wherein $R^{18}$, $R^{19}$, $R^{20}$, $R^{21}$, $R^{22}$, $R^{23}$, $R^{24}$, and $R^{25}$ are each independently selected from H and $C_1$ to $C_5$ alkyl groups. In more particular embodiments, the catalyst compounds, according to Formula II, $R^{27}$, $R^{28}$, $R^{29}$, $R^{30}$, $R^{31}$, $R^{32}$, $R^{33}$, and $R^{34}$, are each independently selected from H and $C_1$ to $C_5$ alkyl groups; particularly, wherein Y is a divalent $C_1$ to $C_5$ hydrocarbyl radical, particularly, —($CH_2CH_2$)—; and, optionally, wherein at least one of $X^1$ and/or $X^2$ is selected from $C_6$ to $C_{15}$ aryl groups, particularly benzyl.

In some embodiments, at least one of $R^{*1}$ and $R^{*2}$ independently comprises a pyrrole radical having the structure according to Formula IV:

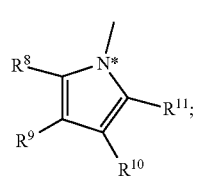

Formula IV wherein:

N* indicates an attachment carbon of the radical; and each of $R^8$, $R^9$, $R^{10}$, $R^{11}$ is, independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), optionally two or more of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof. In particular embodiments, each of $R^{*1}$ and $R^{*2}$ independently comprises a pyrrole radical according to Formula IV.

Some catalyst compounds having features according to Formula I have a structure according to Formula V:

Formula V

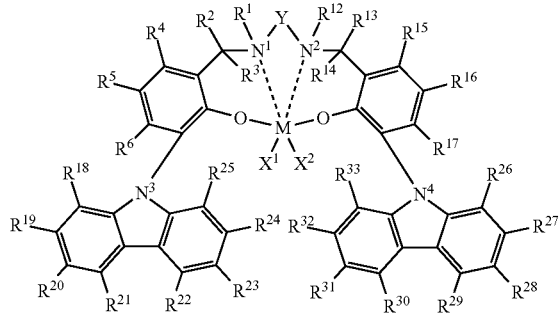

Formula VI

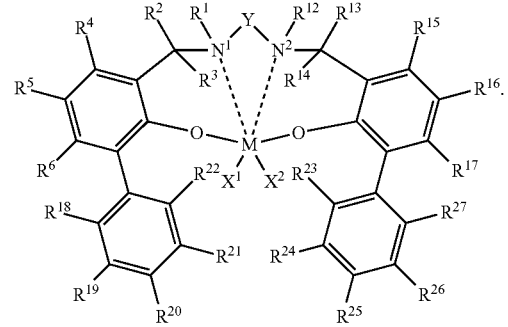

In particular embodiments according to Formula V, $N^3$ and $N^4$ are nitrogen, each $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ is, independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), or two or more of $R^1$ to $R^{33}$ may independently join together to form a $C_4$ to $C_{62}$ cyclic or polycyclic ring structure, or a combination thereof, and M, O, $N^1$, $N^2$, Y, $X^1$, $X^2$, $R^1$-$R^6$, and $R^{12-17}$ are as defined in Formula I. Optionally, at least one of $R^5$ and/or $R^{16}$ is selected from the group consisting of $C_1$ to $C_{10}$ alkyl, $C_1$ to $C_{10}$ alkoxy, and $C_6$ to $C_{15}$ aryl. In some embodiments, each of $R^5$ and $R^{16}$ is independently selected from the group consisting of methyl, ethyl, n-propyl, i-propyl, n-butyl, sec-butyl, i-butyl, t-butyl, methoxy, ethoxy, n-propoxy, i-propoxy, n-butoxy, sec-butoxy, i-butoxy, t-butoxy, phenyl, and $C_1$ to $C_5$ substituted phenyl groups. In some embodiments, the catalyst compounds according to Formula V may have a structure wherein each of $R^1$, $R^2$, $R^3$, $R^4$, $R^6$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$, are each independently selected from H and $C_1$ to $C_5$ alkyl groups. In some embodiments according to Formula V, Y is a divalent $C_1$ to $C_5$ hydrocarbyl radical, particularly —($CH_2CH_2$)—. In other embodiments, Y is a $C_1$-$C_{40}$ divalent hydrocarbyl radical comprising O, S, S(O), S(O)$_2$, Si(R')$_2$, P(R'), N, N(R'), or a combination thereof, wherein each R' is independently a $C_1$ to $C_{18}$ hydrocarbyl radical. Additionally or alternatively, some catalysts according to Formula V have a structure wherein at least one of $X^1$ and/or $X^2$ is selected from the group consisting of a halogen or a $C_1$ to $C_7$ hydrocarbyl radical, and a $C_6$ to $C_{15}$ aryl group, particularly benzyl.

In particular embodiments, the catalyst, according to Formula V, has a structure wherein M is Zr; $X^1$ and $X^2$ are benzyl radicals; $R^1$ and $R^{12}$ are methyl radicals; $R^2$, $R^3$ $R^4$, $R^5$, $R^6$, $R^{13}$, $R^{14}$ $R^{15}$, $R^{17}$, $R^{18}$, $R^{19}$, $R^{20}$, $R^{21}$, $R^{22}$, $R^{23}$, $R^{24}$, and $R^{25}$ are hydrogen; $R^{16}$ is bromine; and Y is —$CH_2CH_2$—.

In other embodiments, the catalyst, according to Formula V, has a structure wherein M is Zr; $X^1$ and $X^2$ are benzyl radicals; $R^1$, $R^{12}$ and $R^{16}$ are methyl radicals; $R^2$, $R^3$ $R^4$, $R^5$, $R^6$, $R^{13}$, $R^{14}$ $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ $R^{32}$, and $R^{33}$ are hydrogen; and Y is —$CH_2CH_2$—.

In particular embodiments, the catalyst composition has a structure according to Formula VI:

In Formula VI, with reference to Formula I, each $R^{18}$, $R^{19}$, $R^{20}$, $R^{21}$, $R^{22}$, $R^{23}$, $R^{24}$, $R^{25}$, $R^{26}$, and $R^{27}$ is, independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), or two or more of $R^1$ to $R^{33}$ may independently join together to form a $C_4$ to $C_{62}$ cyclic or polycyclic ring structure, or a combination thereof, and M, O, $N^1$, $N^2$, Y, $X^1$, $X^2$, $R^1$-$R^6$, and $R^{12}$-$R^{17}$ are as defined in Formula I. In particular embodiments, Y is a divalent $C_1$ to $C_5$ hydrocarbyl radical, particularly —($CH_2CH_2$)—; and wherein at least one of $X^1$ and/or $X^2$ is selected from the group consisting of a halogen or a $C_1$ to $C_7$ hydrocarbyl radical, and a $C_6$ to $C_{15}$ aryl group, particularly benzyl.

Preferably, M is Hf, Ti, Zr, or mixtures thereof. In some embodiments, Hf is particularly useful. In other embodiments, Zr is particularly useful. In still other embodiments, Ti may be particularly useful.

In some embodiments, the catalyst, according to Formula VI, has a structure wherein each of $X^1$ and $X^2$ is, independently, a halogen or a $C_1$ to $C_7$ hydrocarbyl radical. In particular embodiments, each of $X^1$ and $X^2$ is a benzyl radical.

In particular embodiments, catalysts, according to Formula VI, have a structure wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, hydrogen, a halogen, or a $C_1$ to $C_{30}$ hydrocarbyl radical, particularly a $C_1$ to $C_{10}$ hydrocarbyl radical. In some such embodiments, one or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is a methyl radical, a fluoride, or a combination thereof.

Additionally or alternatively, in some embodiments, Y may be —$CH_2CH_2$— or 1,2-cyclohexylene. In other embodiments, Y may be —$CH_2CH_2CH_2$—. In other embodiments, catalysts, according to Formula VI, have a structure wherein Y is a $C_1$ to $C_{40}$ divalent hydrocarbyl radical comprising a linker backbone comprising from 1 to 18 carbon atoms bridging between nitrogen atoms $N^1$ and $N^2$. In some particular embodiments, Y may be a $C_1$ to $C_{40}$ divalent hydrocarbyl radical comprising O, S, S(O), S(O)$_2$, Si(R')$_2$, P(R'), N, N(R'), or a combination thereof, wherein each R' is independently a $C_1$ to $C_{18}$ hydrocarbyl radical.

In some certain catalyst compounds according to Formula VI, M is Ti; $X^1$ and $X^2$ are benzyl radicals; $R^1$ and $R^{12}$ are methyl radicals; $R^2$, $R^3$, $R^4$, $R^6$, $R^{13}$, $R^{14}$, $R^{15}$, $R^{16}$ and $R^{17}$ are hydrogen; $R^5$, $R^{16}$, $R^{18}$, $R^{19}$, $R^{20}$, $R^{21}$, $R^{22}$, $R^{23}$, $R^{24}$, $R^{25}$, $R^{26}$, and $R^{27}$ are fluorine; and Y is —$CH_2CH_2$—.

In some embodiments, certain catalyst compounds according to Formula VI have a structure wherein M is Ti; $X^1$ and $X^2$ are benzyl radicals; $R^1$, $R^5$, $R^{12}$ and $R^{16}$ are methyl radicals; $R^2$, $R^3$, $R^4$, $R^6$, $R^{13}$, $R^{14}$, $R^{15}$, and $R^{17}$ are hydrogen; $R^{18}$, $R^{19}$, $R^{20}$, $R^{21}$, $R^{22}$, $R^{23}$, $R^{24}$, $R^{25}$, $R^{26}$, and $R^{27}$ are fluorine; and Y is —$CH_2CH_2$—.

In still other embodiments, certain catalyst compounds, according to Formula VI, have a structure wherein M is Zr; $X^1$ and $X^2$ are benzyl radicals; $R^1$ and $R^{12}$ are methyl radicals; $R^2$, $R^3$, $R^4$, $R^6$, $R^{13}$, $R^{14}$, $R^{15}$, and $R^{17}$ are hydrogen; $R^5$, $R^{16}$, $R^{18}$, $R^{19}$, $R^{20}$, $R^{21}$, $R^{22}$, $R^{23}$, $R^{24}$, $R^{25}$, $R^{26}$, and $R^{27}$ are fluorine; and Y is —$CH_2CH_2$—.

In still other embodiments, certain catalyst compounds, according to Formula VI, have a structure wherein M is Zr; $X^1$ and $X^2$ are benzyl radicals; $R^1$, $R^5$, $R^{16}$ and $R^{16}$ are methyl radicals; $R^2$, $R^3$, $R^4$, $R^6$, $R^{12}$, $R^{14}$, $R^{15}$, and $R^{17}$ are hydrogen; $R^{18}$, $R^{19}$, $R^{20}$, $R^{21}$, $R^{22}$, $R^{23}$, $R^{24}$, $R^{25}$, $R^{26}$, and $R^{27}$ are fluorine; and Y is —$CH_2CH_2$—.

In still other embodiments, the invention relates to catalysts systems wherein the catalyst, according to Formula I, has a structure according to Formula VII:

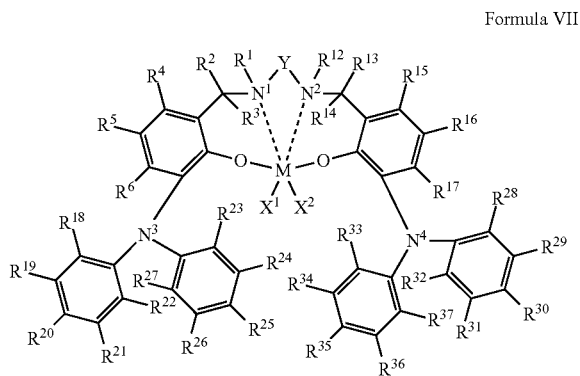

Formula VII

In Formula VII, M may be a Group 3, 4, 5, or 6 transition metal; $N^1$, $N^2$, $N^3$, and $N^4$ are nitrogen; O is oxygen; each of $X^1$ and $X^2$ may be, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure, provided however when M is trivalent $X^2$ is not present; Y is a divalent hydrocarbyl radical covalently bonded to and bridging between both of the nitrogen atoms $N^1$ and $N^2$; and each $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$, is, independently, a hydrogen, a $C_1$ to $C_{40}$ hydrocarbyl radical, a $C_1$ to $C_{40}$ substituted hydrocarbyl radical (such as, a functional group comprising elements from Group 13 to 17 of the periodic table of the elements), or two or more of $R^1$ to $R^{32}$ may independently join together to form a $C_4$ to $C_{62}$ cyclic or polycyclic ring structure wherein neither $R^{18}$ and $R^{22}$ join together with $R^{23}$ or $R^{27}$ to form direct covalent bonds between the respective aromatic rings, and wherein neither $R^{33}$ and $R^{37}$ join together with $R^{28}$ or $R^{32}$ to form direct covalent bonds between the respective aromatic rings, or a combination thereof.

Particular embodiments may have one or more of the following features:

In particular embodiments, M may be Hf, Ti, Zr, or mixtures thereof. In particular embodiments, M is Hf. In other embodiments, M may be Zr. In still other useful embodiments, M may be Ti.

Additionally or alternatively, in some embodiments, each of $X^1$ and $X^2$ is, independently, a halogen or a $C_1$ to $C_7$ hydrocarbyl radical. In particular such embodiments, each of $X^1$ and $X^2$ is a benzyl radical.

Additionally or alternatively, in some embodiments Y may have a certain structure. Thus, in some embodiments, Y may be —$CH_2CH_2$— or 1,2-cyclohexylene. In other embodiments, Y is —$CH_2CH_2CH_2$—. In certain embodiments, Y is a $C_1$ to $C_{40}$ divalent hydrocarbyl radical comprising a linker backbone comprising from 1 to 18 carbon atoms bridging between nitrogen atoms $N^1$ and $N^2$. In particular embodiments, Y is a $C_1$ to $C_{40}$ divalent hydrocarbyl radical comprising O, S, S(O), S(O)$_2$, Si(R')$_2$, P(R'), N, N(R'), or a combination thereof, wherein each R' is independently a $C_1$ to $C_{18}$ hydrocarbyl radical.

Certain catalysts, according to Formula VII, have a structure wherein each $R^1$, $R^2$, $R^3$, $R^4$, $R^5$, $R^6$, $R^{12}$, $R^{13}$, $R^{14}$, $R^{15}$, $R^{16}$, $R^{17}$, $R^{19}$, $R^{20}$, $R^{21}$, $R^{24}$, $R^{25}$, $R^{26}$, $R^{29}$, $R^{30}$, $R^{31}$, $R^{34}$, $R^{35}$, and $R^{36}$ is, independently, a hydrogen, a $C_1$ to $C_{40}$ hydrocarbyl radical, a functional group comprising elements from Groups 13 to 17 of the periodic table of the elements, or two or more of $R^1$, $R^2$, $R^3$, $R^4$, $R^5$, $R^6$, $R^{12}$, $R^{13}$, $R^{14}$, $R^{15}$, $R^{16}$, $R^{17}$, $R^{19}$, $R^{20}$, $R^{21}$, $R^{24}$, $R^{25}$, $R^{26}$, $R^{29}$, $R^{30}$, $R^{31}$, $R^{34}$, $R^{35}$, and $R^{36}$ may independently join together to form a $C_4$ to $C_{62}$ cyclic or polycyclic ring structure, or a combination thereof; and each $R^{18}$, $R^{22}$, $R^{23}$, $R^{27}$, $R^{28}$, $R^{32}$, $R^{33}$, and $R^{37}$ and is, independently, a hydrogen, a $C_1$ to $C_{40}$ hydrocarbyl radical, a functional group comprising elements from Groups 13 to 17 of the periodic table of the elements, or a combination thereof.

In some embodiments, catalyst compounds, according to Formula VII, have a structure wherein each $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ is, independently, hydrogen, a halogen, or a $C_1$ to $C_{30}$ hydrocarbyl radical, more particularly a $C_1$ to $C_{10}$ hydrocarbyl radical. In particular embodiments, the catalysts according to Formula XI have a structure wherein one or more of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ is a methyl radical, a fluoride, or a combination thereof.

In certain embodiments, catalyst compounds, according to Formula VII, have a structure wherein $R^{22}$ and $R^{27}$ join together to form a divalent $C_1$ to $C_{20}$ hydrocarbyl radical, a divalent functional group comprising elements from Groups 13 to 16 of the periodic table of the elements, or a combination thereof, and wherein $R^{32}$ and $R^{37}$ join together to form a divalent $C_1$ to $C_{20}$ hydrocarbyl radical, a divalent functional group comprising elements from Groups 13 to 16 of the periodic table of the elements, or a combination thereof.

In particular embodiments, catalyst compounds, according to Formula VII, may have a structure wherein:

M is Zr;
$X^1$ and $X^2$ are benzyl radicals;
$R^1$ and $R^{12}$ are methyl radicals;
$R^2$, $R^3$, $R^4$, $R^5$, $R^6$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ are hydrogen; and
Y is —$CH_2CH_2$—.

In other embodiments, catalyst compounds, according to Formula VII, may have a structure wherein:

M is Zr;
$X^1$ and $X^2$ are benzyl radicals;
$R^1$, $R^5$, $R^{12}$, and $R^{16}$ are methyl radicals;
$R^2$, $R^3$, $R^4$, $R^6$, $R^{13}$, $R^{14}$, $R^{15}$, $R^{17}$ to $R^{37}$ are hydrogen; and
Y is —$CH_2CH_2$—.

In still other embodiments, catalyst compounds, according to Formula VII, have a structure according to Formula VIII:

Formula VIII

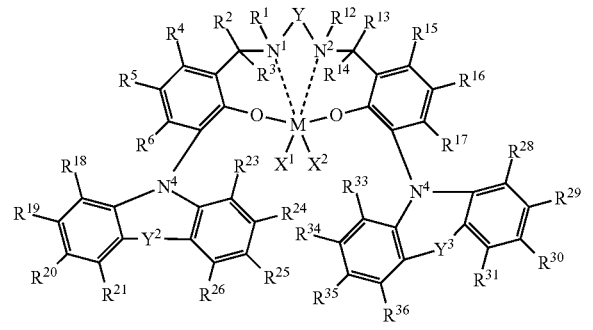

As described in Formula VII or in Formula VIII, O is oxygen;

M may be a Group 3, 4, 5, or 6 transition metal;

$N^1$, $N^2$, $N^3$, and $N^4$ are nitrogen;

each of $X^1$ and $X^2$ is, independently, a univalent $C_1$ to $C_{20}$ hydrocarbyl radical, a $C_1$ to $C_{40}$ substituted hydrocarbyl radical (such as, a functional group comprising elements from Groups 13 to 17 of the periodic table of the elements), or $X^1$ and $X^2$ join together to form a $C_4$ to $C_{62}$ cyclic or polycyclic ring structure, provided, however, when M is trivalent $X^2$ is not present; and Y is a divalent $C_1$ to $C_{20}$ hydrocarbyl radical; $Y^2$ and $Y^3$ are independently a divalent $C_1$ to $C_{20}$ hydrocarbyl radical, a $C_1$ to $C_{20}$ substituted hydrocarbyl radical (such as a divalent functional group comprising elements from Groups 13 to 16 of the periodic table of the elements), or a combination thereof; and each $R^1$ to $R^6$, $R^{12}$ to $R^{21}$, $R^{23}$ to $R^{26}$, $R^{28}$ to $R^{31}$, and $R^{33}$ to $R^{36}$ is, independently, a hydrogen, a $C_1$ to $C_{40}$ hydrocarbyl radical is, a $C_1$ to $C_{40}$ substituted hydrocarbyl radical (such as a functional group comprising elements from Groups 13 to 17 of the periodic table of the elements), or two or more of $R^1$ to $R^6$, $R^{12}$ to $R^{21}$, $R^{23}$ to $R^{26}$, $R^{28}$ to $R^{31}$, and $R^{33}$ to $R^{36}$ may independently join together to form a $C_4$ to $C_{62}$ cyclic or polycyclic ring structure.

Certain useful catalyst compositions are also described in U.S. Application 61/679,488, filed Aug. 3, 2012; Ser. No. 13/921,532, filed Jun. 19, 2013; 61/679,505, filed Aug. 3, 2012; Ser. No. 13/921,709, filed Jun. 19, 2013; 61/679,527, filed Aug. 3, 2012; Ser. No. 13/921,761, filed Jun. 19, 2013; 61/722,110, filed Nov. 2, 2012; Ser. No. 14/059,081, filed Oct. 21, 2013; 61/779,435, filed Mar. 13, 2013; 61/837,593, filed Jun. 20, 2013; Ser. No. 14/076,750, filed Nov. 11, 2013; 61/837,554, filed Jun. 20, 2013; Ser. No. 14/289,075, filed May 28, 2014; 61/837,569, filed Jun. 20, 2013; Ser. No. 14/298,575, filed Jun. 6, 2014; 61/837,588, filed Jun. 20, 2013; Ser. No. 14/289,186, filed May 28, 2014; 61/982,823, filed Apr. 22, 2014; and Ser. No. 14/557,813 filed Dec. 2, 2014, each of which is incorporated herein by reference.

Methods to Prepare the Catalyst Compounds

In embodiments of the invention, the symmetric transition metal compounds may be prepared by two general synthetic routes. The parent Satan ligands are prepared by a one-step Mannich reaction from the parent phenol (Reaction A) or by a two-step imine-condensation/alkylation procedure if the salicylaldehyde is used (Reaction B). The ligand is then converted into the metal dibenzyl catalyst precursor by reaction with the metal tetra-aryl starting material, (e.g., tetrabenzyl), to yield the finished complex (Reaction C).

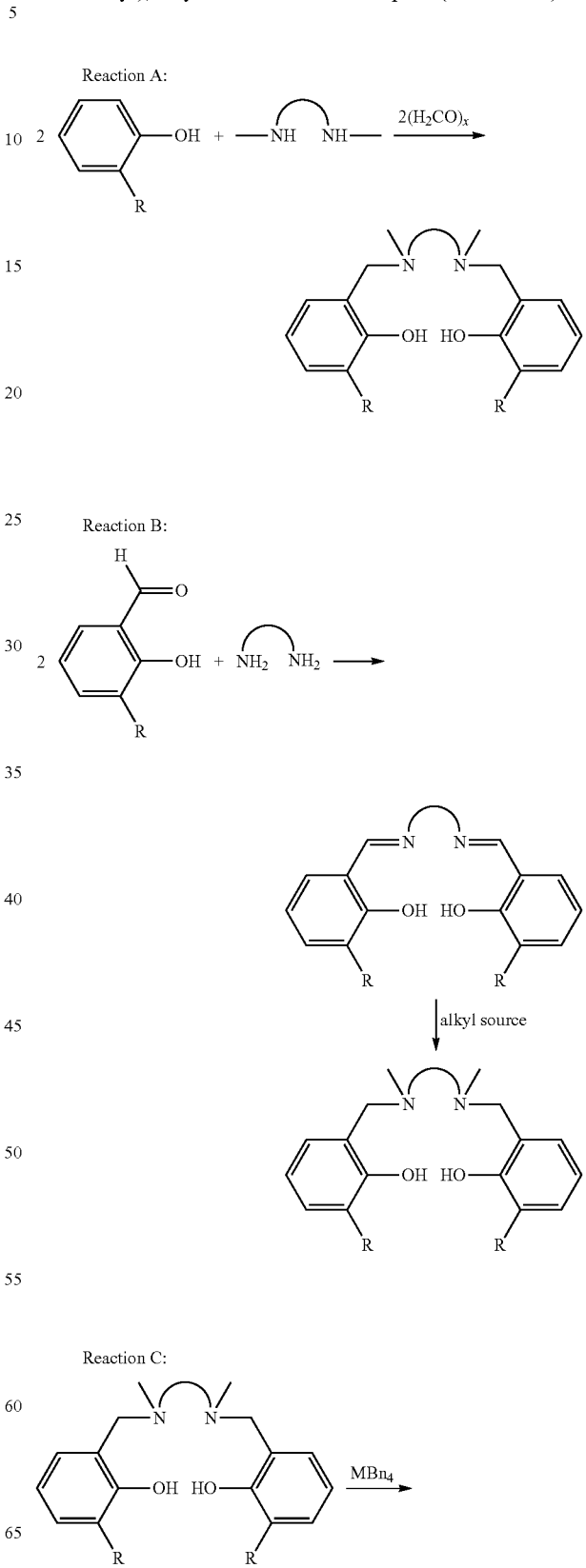

-continued

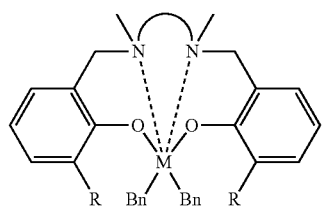

Asymmetric transition metal compounds may be prepared by a step-wise synthetic route. The parent Salan ligands are prepared by reaction of the salicylaldehyde with the diamine, followed by reduction with NaBH$_4$. The asymmetric ligand is then formed by an HBr elimination reaction with a bromomethylphenol (Reaction D). The ligand is then converted into the metal dibenzyl catalyst precursor by reaction with the metal tetrabenzyl starting material to yield the finished complex (Reaction E).

Reaction D:

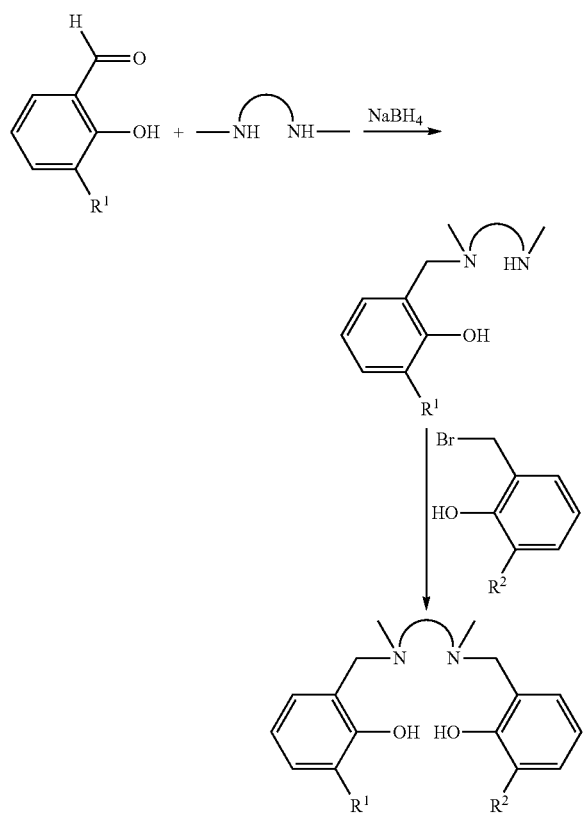

Reaction E:

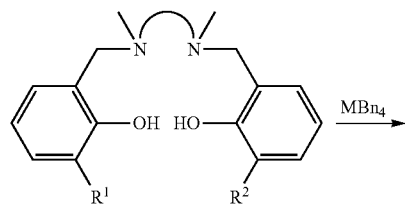

-continued

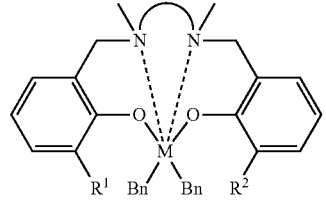

Activators

The terms "cocatalyst" and "activator" are used interchangeably to describe activators and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Activators may include alumoxane compounds, modified alumoxane compounds, and ionizing anion precursor compounds that abstract a reactive, σ-bound, metal ligand making the metal complex cationic and providing a charge-balancing non-coordinating or weakly coordinating anion.

In one embodiment, alumoxane activators are utilized as an activator in the catalyst composition. Alumoxanes are generally oligomeric compounds containing —Al($R^1$)—O— sub-units, where $R^1$ is an alkyl radical. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the catalyst precursor compound comprises an abstractable ligand which is an alkyl, halide, alkoxide, or amide. Mixtures of different alumoxanes and modified alumoxanes may also be used. In an embodiment, visually clear methylalumoxane may be used. A cloudy or gelled alumoxane can be filtered to produce a clear solution or clear alumoxane can be decanted from the cloudy solution. A useful alumoxane is a modified methyl alumoxane (MMAO) described in U.S. Pat. No. 5,041,584 and/or commercially available from Akzo Chemicals, Inc., under the trade designation Modified Methylalumoxane type 3A. Solid alumoxanes may also be used.

In an embodiment, the activator is a TMA-depleted activator (where TMA is the abbreviation for trimethylaluminum). The inventors have advantageously found that using a TMA-depleted alkyl alumoxane contributes to producing a polymer with higher allyl chain ends. Commercial alumoxanes, such as methylalumoxane (MAO) and isobuylalumoxane, often tend to comprise some residual starting material as an impurity. For example, one common method of making MAO is the hydrolysis of trimethylaluminum (TMA). Such hydrolysis, however, tends to leave residual TMA in the MAO which may have negative effects on polymerization. Any methods known in the art to remove TMA may be used. In an embodiment, for example, to produce a TMA-depleted activator, a solution of alumoxane (such as methylalumoxane), for example, 30 wt % in toluene may be diluted in toluene and the aluminum alkyl (such as TMA in the case of MAO) is removed from the solution, for example, by combination with trimethylphenol and filtration of the solid. In an embodiment, the TMA-depleted activator comprises from about 1 wt % to about 14 wt % trimethylaluminum, or less than 13 wt %, or less than 12 wt %, or less than 10 wt %, or less than 5 wt %, or 0 wt %, and/or, greater than 0 wt %, or greater than 1 wt %.

When the activator is an alumoxane (modified or unmodified), in an embodiment, the maximum amount of activator is a 5000-fold molar excess Al/M over the catalyst compound (per metal catalytic site). In an embodiment, the minimum activator-to-catalyst-compound, which is determined according to molar concentration of the transition metal M in an embodiment, is 1 mole aluminum or less to mole of transition metal M. In an embodiment, the activator comprises alumoxane and the alumoxane is present at a ratio of 1 mole aluminum or more to mole of catalyst compound. In an embodiment, the minimum activator-to-catalyst-compound molar ratio is a 1:1 molar ratio. Other embodiments of Al:M ranges include from 1:1 to 500:1, or from 1:1 to 200:1, or from 1:1 to 100:1, or from 1:1 to 50:1.

In an embodiment, little or no non-coordinating anion activator (NCA) (i.e., less than 0.001 wt %) is used in the polymerization processes described herein. In an embodiment, NCA is present at 0.00 mol %, or the NCA is present at a molar ratio of NCA metal to catalyst compound transition metal less than 500:1, or less than 300:1, or less than 100:1, or less than 1:1.

When the activator is an alumoxane (modified or unmodified), in an embodiment, the maximum amount of activator is a 5000-fold molar excess Al/M over the catalyst compound (per metal catalytic site). In an embodiment, the minimum activator-to-catalyst-compound, which is determined according to molar concentration of the transition metal M, in an embodiment is 1 mole aluminum or less to mole of transition metal M. In an embodiment, the activator comprises alumoxane and the alumoxane is present at a ratio of 1 mole aluminum or more to mole of catalyst compound. In an embodiment, the minimum activator-to-catalyst-compound molar ratio is a 1:1 molar ratio. Other embodiments of Al:M ranges include from 1:1 to 500:1, or from 1:1 to 200:1, or from 1:1 to 100:1, or from 1:1 to 50:1.

In an embodiment, little or no alumoxane (i.e., less than 0.001 wt %) is used in the polymerization processes described herein. In an embodiment, alumoxane is present at 0.00 mol %, or the alumoxane is present at a molar ratio of aluminum to catalyst compound transition metal less than 500:1, or less than 300:1, or less than 100:1, or less than 1:1.

Examples of neutral stoichiometric activators include tri-substituted boron, tellurium, aluminum, gallium, and indium, or mixtures thereof. The three substituent groups or radicals can be the same or different and in an embodiment are each independently selected from substituted or unsubstituted alkyls, alkenyls, alkyns, aryls, alkoxy, and halogens. In an embodiment, the three groups are independently selected from halogen, mono or multicyclic (including halosubstituted) aryls, alkyls, and alkenyl compounds, and mixtures thereof; or independently selected from alkenyl radicals having 1 to 20 carbon atoms, alkyl radicals having 1 to 20 carbon atoms, alkoxy radicals having 1 to 20 carbon atoms and aryl or substituted aryl radicals having 3 to 20 carbon atoms. In an embodiment, the three substituent groups are alkyl radicals having 1 to 20 carbon atoms, phenyl, naphthyl, or mixtures thereof. In an embodiment, the three groups are halogenated aryl groups, e.g., fluorinated aryl groups. In an embodiment the neutral stoichiometric activator is tris-perfluorophenyl boron or tris perfluoronaphthyl boron.

In an embodiment, ionic stoichiometric activator compounds may include an active proton, or some other cation associated with, but not coordinated to, or only loosely coordinated to the remaining ion of the ionizing compound. Suitable examples include compounds and the like described in EP 0 570 982 A1; EP 0 520 732 A1; EP 0 495 375 A1; EP 0 500 944 B1; EP 0 277 003 A1; EP 0 277 004 A1; U.S. Pat. Nos. 5,153,157; 5,198,401; 5,066,741; 5,206,197; 5,241,025; 5,384,299; 5,502,124; and WO 1996/04319; all of which are fully incorporated herein by reference.

In an embodiment compounds useful as an activator comprise a cation, which is, for example, a Bronsted acid capable of donating a proton, and a compatible non-coordinating anion which anion is relatively large (bulky), capable of stabilizing the active catalyst species (the Group 4 cation, e.g.) which is formed when the two compounds are combined and said anion will be sufficiently labile to be displaced by olefinic, diolefinic, or acetylenically unsaturated substrates or other neutral Lewis bases, such as ethers, amines, and the like. Two classes of useful compatible non-coordinating anions are disclosed in EP 0 277 003 A1, and EP 0 277 004 A1, which include anionic coordination complexes comprising a plurality of lipophilic radicals covalently coordinated to and shielding a central charge-bearing metal or metalloid core; and anions comprising a plurality of boron atoms such as carboranes, metallacarboranes, and boranes.

In an embodiment, the stoichiometric activators include a cation and an anion component, and may be represented by the following formula (1):

$$(Z)_d^+(A^{d-}) \tag{1}$$

wherein:

Z is (L-H) or a reducible Lewis Acid, L is a neutral Lewis base; H is hydrogen; (L-H)$^+$ is a Bronsted acid; $A^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the catalyst precursor, resulting in a cationic transition metal species, or the activating cation (L-H)$_d^+$ is a Bronsted acid, capable of donating a proton to the catalyst precursor resulting in a transition metal cation, including ammoniums, oxoniums, phosphoniums, syliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it may be represented by the formula: (Ar$_3$C$^+$), where Ar is aryl or aryl substituted with a heteroatom, or a $C_1$ to $C_{40}$ hydrocarbyl, the reducible Lewis acid may be represented by the formula: (Ph$_3$C$^+$), where Ph is phenyl or phenyl substituted with a heteroatom, and/or a $C_1$ to $C_{40}$ hydrocarbyl. In an embodiment, the reducible Lewis acid is triphenyl carbenium.

Embodiments of the anion component $A^{d-}$ include those having the formula [M$^{k+}$Q$_n$]$^{d-}$ wherein k is 1, 2, or 3; n is 1, 2, 3, 4, 5, or 6, or 3, 4, 5, or 6; n−k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable $A^{d-}$ components also include diboron compounds as disclosed in U.S. Pat. No. 5,447,895, which is fully incorporated herein by reference.

Scavengers or Co-Activators

In an embodiment, the catalyst system may further include scavengers and/or co-activators. Suitable aluminum alkyl or organoaluminum compounds, which may be utilized as scavengers or co-activators include, for example, trimethylaluminum, triethylaluminum, triisobutylaluminum, tri-n-hexylaluminum, tri-n-octylaluminum, and the like. Other oxophilic species such as diethyl zinc may be used. In an embodiment, the scavengers and/or co-activators are present at less than 14 wt %, or from 0.1 to 10 wt %, or from 0.5 to 7 wt %, by weight of the catalyst system.

Fluorided Supports

As used herein, the phrases "fluorided support" and "fluorided support composition" mean a support, desirably particulate and porous, which has been treated with at least one inorganic fluorine-containing compound. For example, the fluorided support composition can be a silicon dioxide support wherein a portion of the silica hydroxyl groups has been replaced with fluorine or fluorine-containing compounds. Likewise, the term "support composition" means a support, desirably particulate and porous, which has been treated with at least one fluorine-containing compound. Suitable fluorine-containing compounds include, but are not limited to, inorganic fluorine-containing compounds and/or organic fluorine-containing compounds.

Supports suitable for use in this invention are generally porous materials and can include organic materials, inorganic materials, and inorganic oxides. Desirably, supports suitable for use in this invention include talc, clay, silica, alumina, magnesia, zirconia, iron oxides, boria, calcium oxide, zinc oxide, barium oxide, thoria, aluminum phosphate gel, polyvinylchloride and substituted polystyrene, and mixtures thereof. Other useful support materials include zeolites, clays, organoclays, or any other organic or inorganic support material and the like, or mixtures thereof.

Preferably, the support material is an inorganic oxide in a finely divided form. Suitable inorganic oxide materials for use in the catalyst systems described herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2$/$Al_2O_3$. In a preferred embodiment of the invention, the support is silica.

It is preferred that the support material, preferably an inorganic oxide, preferably silica, has a surface area in the range of from about 10 to about 800 $m^2$/g (alternately about 10 to about 700 $m^2$/g), pore volume in the range of from about 0.1 to about 4.0 cc/g and average particle size in the range of from about 5 to about 500 μm. More preferably, the surface area of the support material is in the range of from about 50 to about 500 $m^2$/g, pore volume of from about 0.5 to about 3.5 cc/g and average particle size of from about 10 to about 200 μm. Most preferably the surface area of the support material is in the range of from about 100 to about 400 $m^2$/g, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2$/gm; pore volume of 1.65 $cm^3$/gm). Useful silicas are available under the trade names of DAVISON™ 952, DAVISON™ 948, or DAVISON™ 955 by the Davison Chemical Division of W.R. Grace and Company. Total surface area, also referred to as "surface area" and total pore volume, also referred to as "pore volume," and average pore diameter, also referred to as average pore size, are measured by the Brunauer-Emmett-Teller (BET) method using adsorption-desorption of nitrogen (temperature of liquid nitrogen, 77 K) with a Micromeritics Tristar II 3020 instrument after degassing of the powders for 4 hrs at 350° C. More information regarding the method can be found, for example, in "*Characterization of Porous Solids and Powders: Surface Area, Pore Size and Density*", S. Lowell et al., Springer, 2004. Average particle size, also referred to as "particle size," or "particle diameter" is determined using a Mastersizer™ 3000 (range of 1 to 3500 μm) available from Malvern Instruments, Ltd., Worcestershire, England.

In a particularly useful embodiment, the support is silica, is desirably porous and has a surface area in the range of from about 10 to about 800 $m^2$/g, a total pore volume in the range of from about 0.1 to about 4.0 cc/g and an average particle diameter in the range of from about 10 to about 500 μm. More desirably, the surface area is in the range of from about 50 to about 500 $m^2$/g, the pore volume is in the range of from about 0.5 to about 3.5 cc/g and the average particle diameter is in the range of from about 15 to about 150 μm. Most desirably the surface area is in the range of from about 100 to about 400 $m^2$/g, the pore volume is in the range of from about 0.8 to about 3.0 cc/g and the average particle diameter is in the range of from about 20 to about 100 μm. The average pore diameter of typical porous silicon dioxide support materials is in the range of from about 10 to about 1000 Å. Desirably, the support material has an average pore diameter of from about 50 to about 500 Å, and most desirably from about 75 to about 350 Å.

The fluorine compounds suitable for providing fluorine for the support may be organic or inorganic fluorine compounds and are desirably inorganic fluorine-containing compounds. Such inorganic fluorine-containing compounds may be any compound containing a fluorine atom as long as it does not contain a carbon atom. Particularly desirable are inorganic fluorine containing compounds are selected from the group consisting of $NH_4BF_4$, $(NH_4)_2SiF_6$, $NR_4PF_6$, $NH_4F$, $(NH_4)_2TaF_7$, $NH_4NbF_4$, $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_5$, $BrF_5$, $IF_7$, $NF_3$, $HF$, $BF_3$, $NHF_2$, and $NH_4HF_2$. Of these, ammonium hexafluorosilicate and ammonium tetrafluoroborate are useful. Combinations of these compounds may also be used.

Ammonium hexafluorosilicate and ammonium tetrafluoroborate fluorine compounds are typically solid particulates as are the silicon dioxide supports. Typically, the fluorided supports described herein are prepared by combining an aqueous solution of fluorinating agent (such as $SiF_4$ or $(NH_4)_2SiF_6$) with a slurry of support (such as a toluene slurry of silica), then drying until it is free flowing, and, optionally, calcining (typically at temperatures over 100° C.

for at least 1 hour). The supports are then combined with activator(s) and catalyst compounds (separately or together).

A useful method of treating the support with the fluorine compound is to dry mix the two components by simply blending at a concentration of from 0.01 to 10.0 millimole F/g of support, desirably in the range of from 0.05 to 6.0 millimole F/g of support, and most desirably in the range of from 0.1 to 3.0 millimole F/g of support. The fluorine compound can be dry mixed with the support either before or after charging to a vessel for dehydration or calcining the support. Accordingly, the fluorine concentration present on the support is preferably in the range of from 0.1 to 25 wt %, alternately 0.19 to 19 wt %, alternately from 0.6 to 3.5 wt %, based upon the weight of the support.

Another method of treating the support with the fluorine compound is to dissolve the fluorine compound in a solvent, such as water, and then contact the support (dry or combined with water or hydrocarbon solvent) with the fluorine compound containing solution. When water is used and silica is the support, it is desirable to use a quantity of water which is less than the total pore volume of the support.

A disadvantage of typical dry mix methods is that the density difference between fluorinating agent (such as ammonium hexafluorosilicate—density about 2.1 g/cm$^3$) and silica (e.g., such as Davison™ 948—density about 0.7 g/cm$^3$) makes it difficult to evenly/homogeneously distribute the fluorinating agent in the silica support. The density difference has also led to settling of ammonium hexafluorosilicate in fluorided silica derived from dry mix method. Over a period of two weeks, a vertical gradient of ammonium hexafluorosilicate concentrations in fluorided silica (made via dry mix method) stored in a bottle is observed. Such settling can lead to operational problems on a commercial scale.

To overcome these problems, an alternative method (wet-mixing) has been developed. The aqueous (wet-mixing) method employs a minimal amount of a polar solvent (e.g., water, methanol, ethanol, isopropanol, or any solvent capable of dissolving the fluoride compound (such as ammonium hexafluorosilicate) to dissolve the fluorinating agent (e.g., ammonium hexafluorosilicate)). The fluoride compound solution (such as an ammonium hexafluorosilicate solution) is then added to a slurry of silica in anon-polar solvent (e.g., toluene, or benzene, chloroform, etc.), followed by vigorous stirring of the resulting mixture. The polar/hydrophilic nature of the fluoride compound (such as ammonium hexafluorosilicate) leads to its absorption onto the hydrophilic silica surface. When the non-polar solvent is removed (by filtration), silica with an even distribution of fluorinating agent (such as ammonium hexafluorosilicate) is obtained, and ready for subsequent drying and calcination steps.

This method reduces or eliminates non-homogeneous distribution of fluorinating agent in silica associated with other methods. In addition, fluorided silica prepared via wet-mixing method gave excellent operability, whereas fluorided silica prepared via dry-mixing method often gave poor operability due to frequent plugging of catalyst feed line.

Dehydration or calcining of the silica is not necessary prior to reaction with the fluorine compound, but can be done if desired. Desirably, the reaction between the silica and fluorine compound is carried out at a temperature of from about 100° C. to about 400° C., and more desirably from about 150° C. to about 350° C. for about two to eight hours.

In one embodiment, the fluorided support composition may be generically represented by the formula: Sup-F, where "Sup" is a support, and "F" is a fluorine atom bound to the support. The fluorine atom may be bound, directly or indirectly, chemically or physically to the support. An example of chemical or physical bonding would be covalent and ionic bonding, respectively.

In another embodiment, the fluorided support composition is represented by the formula: Sup-LF$_n$, where "Sup" is a support, preferably selected from the group consisting of talc, clay, silica, alumina, magnesia, zirconia, iron oxides, boria, calcium oxide, zinc oxide, barium oxide, thoria, aluminum phosphate gel, polyvinylchloride, and substituted polystyrene; "L" is a first member selected from the group consisting of (i) bonding, sufficient to bound the F to the Sup; (ii) B, Ta, Nb, Ge, Ga, Sn, Si, P, Ti, Mo, Re, Al, or Zr bound to the Sup and to the F; and (iii) O bound to the Sup and bound to a second member selected from the group consisting of B, Ta, Nb, Ge, Ga, Sn, Si, P, Ti, Mo, Re, Al, or Zr which is bound to the F; "F" is a fluorine atom; and "n" is a number from 1-7.

An example of such bonding sufficient to bound the F to the Sup would be chemical or physical bonding, such as, for example, covalent and ionic bonding.

The fluorided support material is then typically slurried in a non-polar solvent and the resulting slurry is contacted with a solution of catalyst compounds and activator. In some embodiments, the slurry of the fluorided support material is first contacted with the activator for a period of time in the range of from about 0.5 hours to about 24 hours, from about 1 hour to about 16 hours, or from about 2 hours to about 8 hours. The solution of the catalyst compound is then contacted with the isolated fluorided support/activator. In some embodiments, the supported catalyst system is generated in situ. In an alternate embodiment, the slurry of the fluorided support material is first contacted with the catalyst compound for a period of time in the range of from about 0.5 hours to about 24 hours, from about 1 hour (or 2 hours) to about 16 hours, or from about 2 hours (or 4 hours) to about 8 hours. The slurry of the supported catalyst compound is then contacted with the activator solution.

The mixture of the catalysts, activator and fluorided support may be heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

In a preferred embodiment of the invention, the fluorided support material is slurried in a non-polar solvent and the resulting slurry is contacted with a solution of methylalumoxane (typically 30 wt % MAO in toluene). The fluorided support/MAO mixture is then heated to elevated temperature (30° C. to 120° C., preferably 80 to 100° C.) with vigorous stirring for a period of time (0.1 to 24 hours, preferably 1 to 3 hours). The support/activator is isolated by filtration, rinsed with non-polar solvent (e.g., toluene, pentane, hexane, etc.), and dried. The isolated support/activator is then slurried in a non-polar solvent (e.g., toluene), and a solution of catalyst compound/compounds is then contacted with the support/activator slurry. Vigorous stirring may then be applied.

In a preferred embodiment of the invention, the fluorided support material is slowly added in solid form to a solution of MAO in non-polar solvent (e.g., toluene) (typically at room temperature) with vigorous stirring. This addition sequence, namely slow and portion-wise addition of fluorided silica to MAO solution, is referred to as "reversed addition." After the addition of fluorided silica is completed, the fluorided support/MAO mixture is then heated to elevated temperature (30° C. to 120° C., preferably 80 to 100° C.) with vigorous stirring for a period of time (0.1 to 24 hours, preferably 1 to 3 hours). The support/activator is isolated by filtration, rinsed with non-polar solvent (e.g., toluene, pentane, hexane, etc.), and dried. The isolated support/activator is then slurried in a non-polar solvent (e.g., toluene), and a solution of catalyst compound/compounds is then contacted with the support/activator slurry. Vigorous stirring may be applied.

Under otherwise identical conditions, the "reversed addition" method for immobilizing MAO on fluorided silica surface offers higher polymerization activity for a wide variety of catalysts, compared to the "traditional addition" method where MAO solution is added to a slurry of fluorided silica in non-polar solvent.

Suitable "non-polar solvents" are materials in which all of the reactants used herein, i.e., the activator, and the catalyst compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

In a preferred embodiment of the invention, the fluorided supports described herein are prepared by combining an aqueous solution of fluorinating agent (such as $(NH_4)_2SiF_6$) with a slurry of support (such as a toluene slurry of silica), drying until free flowing, optionally, calcining (typically at temperatures from 100° C. to 400° C. for at least 1 hour), then combining with activators and catalyst compounds (the activators and catalyst compounds may be added to the support separately or together).

In another embodiment of the invention, the water to solvent ratio (by weight) is between 1:10 to 1:1000, preferably between 1:20 to 1:50.

In another embodiment of the invention, the fluorided silica support can immobilize greater than 5.0 mmol "Al" per gram silica, and preferably greater than 6.0 mmol "Al"/gram silica. The amount of "Al" (from alkylalumoxane, such as MAO) that can be immobilized on 1 gram of fluorided silica is determined by an aluminum titration experiment. The titration is done at 100° C. at ambient pressure allowing the alumoxane (15 mmol Al) and the 1 gram of fluorided silica to react for 3 hours. Thereafter, the silica is washed with toluene (10 ml, 3 times) and then washed with pentane (10 ml, 3 times). The solid is then collected and dried under vacuum for 8 hours until solvent is removed. Then the sample is weighed and the difference in weight is divided by the Mw of the aluminum compound (Mw as reported in the CHEMICAL AND ENGINEERING NEWS, 63(5), pg. 27, (1985)). Methyl alumoxane is defined to be Me—Al—O. The "Al" uptake for silica-1 in the examples below is about 5.5 mmol Al/gram, whereas the "Al" uptake for silica-2 is about 6.8 mmol/gram. Higher Al uptake (or loading) is often desirable as it is thought to offer higher polymerization activity, provided the silica and the catalyst precursor stay unchanged. In a useful embodiment of the invention, the catalyst system comprising the fluorided silica support immobilizes greater than 5.0 mmol "Al" per gram of silica, and preferably greater than 6.0 mmol "Al" per gram of silica.

Alternately, the fluorided silica support preferably contains less than 0.05 mmol/gram fluorinating agent (such as $(NH_4)_2SiF_6$), preferably less than 0.02 mmol/gram fluorinating agent, as measured by $^1H$ NMR. Unless otherwise indicated, $^1H$ NMR data of non-polymeric compounds is collected at room temperature in a 5 mm probe using either a Bruker or Varian NMR spectrometer operating with a $^1H$ frequency of 500 MHz. Data is recorded using a 30° flip angle RF pulse, 8 scans, with a delay of 5 seconds between pulses. Samples are prepared using approximately 5-10 mg of compound dissolved in approximately 1 mL of an appropriate deuterated solvent. Samples are referenced to residual protium of the solvents at 7.15, 7.24, 5.32, 5.98, and 2.10 for D5-benzene, chloroform, D-dichloromethane, D-1,1,2,2-tetrachloroethane, and $C_6D_5CD_2H$, respectively. Unless stated otherwise, NMR spectroscopic data of polymers is recorded in a 5 mm probe on a Varian NMR spectrometer at 120° C. using a $d_2$-1,1,2,2-tetrachloroethane solution prepared from approximately 20 mg of polymer and 1 mL of solvent using a 30° flip angle RF pulse, 120 scans, with a delay of 5 seconds between pulses.

Alternately, the surface area of the fluorided silica support is greater than 200 $m^2/g$, preferably greater than 250 $m^2/g$, as determined by BET. Alternatively, the surface area of combined fluorided silica support and activator (such as MAO) is greater than 250 $m^2/g$, preferably greater than 350 $m^2/g$, as determined by BET.

In embodiments where $SiF_4$ and/or $(NH_4)_2SiF_6$ is/are the fluoriding agent, immediately after combination of the alkylalumoxane with the fluorided support the combination preferably contains less than 0.04 mmoles per gram of silica (preferably less than 0.02 mmoles, preferably less than 0.01 mmoles) of tetraalkylsilane per gram of support as determined by $^1H$ NMR (where the alkyl is derived from the alkylalumoxane).

In useful embodiments, the ratio of mmol of fluorine per gram of silica in the fluorided support is between 0.1 and 1.5, preferably between 0.2 and 1.2, preferably between 0.4 and 1.0.

For fluorided silica prepared using $(NH_4)_2SiF_6$, the amount of residual $(NH_4)_2SiF_6$ in the silica should be equal or less than 0.04 mmol $(NH_4)_2SiF_6$/g silica, preferably equal or less than 0.02 mmol $(NH_4)_2SiF_6$/g silica, more preferably equal or less than 0.01 mmol $(NH_4)_2SiF_6$/g silica.

Polymerization Processes

In an embodiment, polymerization processes include contacting monomers (such as ethylene and propylene), and optionally comonomers, with a catalyst system comprising an activator and at least one catalyst compound, as described above. In an embodiment, the catalyst compound and activator may be combined in any order, and may be combined prior to contacting with the monomer. In an embodiment, the catalyst compound and/or the activator are combined after contacting with the monomer.

Monomers useful herein include substituted or unsubstituted $C_2$ to $C_{40}$ alpha olefins, or $C_2$ to $C_{20}$ alpha olefins, or $C_2$ to $C_{12}$ alpha olefins, or ethylene, propylene, butene, pentene, hexene, heptene, octene, nonene, decene, undecene, dodecene and isomers thereof. In an embodiment of the invention, the monomer comprises propylene and optional comonomers comprising one or more ethylene or $C_4$ to $C_{40}$ olefins, or $C_4$ to $C_{20}$ olefins, or $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups.

In an embodiment, the monomer comprises ethylene and a comonomer comprising one or more $C_3$ to $C_{40}$ olefins, or $C_4$ to $C_{20}$ olefins, or $C_6$ to $C_{12}$ olefins. The $C_3$ to $C_{40}$ olefin monomers may be linear, branched, or cyclic.

The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, or hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, or norbornene, norbornadiene, and dicyclopentadiene.

In an embodiment, one or more dienes are present in the polymer produced herein at up to 10 wt %, or at 0.00001 to 1.0 wt %, or 0.002 to 0.5 wt %, or 0.003 to 0.2 wt %, based upon the total weight of the composition. In an embodiment, 500 ppm or less of diene is added to the polymerization, or 400 ppm or less, or 300 ppm or less. In an embodiment at least 50 ppm of diene is added to the polymerization, or 100 ppm or more, or 150 ppm or more.

Diolefin monomers useful in this invention include any hydrocarbon structure, or $C_4$ to $C_{30}$, having at least two unsaturated bonds, wherein at least two of the unsaturated bonds are readily incorporated into a polymer by either a stereospecific or a non-stereospecific catalyst(s). In an embodiment, the diolefin monomers may be selected from alpha, omega-diene monomers (i.e., di-vinyl monomers). Preferably, the diolefin monomers are linear di-vinyl monomers, most or those containing from 4 to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes according to the instant disclosure may be carried out in any manner known in the art. Any supported polymerization process known in the art (such as gas phase, slurry phase or bulk phase) can be used. Such processes can be run in a batch, semi-batch, or continuous mode. A bulk process is suitable for use herein, wherein a bulk process is defined to be a process where monomer concentration in all feeds to the reactor is 70 vol % or more. In an embodiment, no solvent or diluent is present or added in the reaction medium, (except for the small amounts used as the carrier for the catalyst system or other additives, or amounts typically found with the monomer; e.g., propane in propylene). In an embodiment, the process is a slurry process. As used herein, the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Alternately the polymerization is not a homogeneous process, where a homogeneous polymerization process is defined to be a process where at least 90 wt % of the product is soluble in the reaction media. Alternately, the polymerization is not a solution process where a solution polymerization process is defined to be a process where the catalyst and the product are soluble in the reaction media.

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkyl substituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In an embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In an embodiment, the solvent is not aromatic, or aromatics are present in the solvent at less than 1 wt %, or less than 0.5 wt %, or less than 0.0 wt %, based upon the weight of the solvents.

In an embodiment, the feed concentration of the monomers and comonomers for the polymerization is 60 vol % solvent or less, or 40 vol % or less, or 20 vol % or less, based on the total volume of the feedstream. Or the polymerization is run in a bulk process.

Polymerizations can be run at any temperature and/or pressure suitable to obtain the desired ethylene polymers. Suitable temperatures and/or pressures include a temperature in the range of from about 0° C. to about 300° C., or from about 20° C. to about 200° C., or from about 35° C. to about 150° C., or from about 50° C. to about 150° C., or from about 40° C. to about 120° C., or from about 45° C. to about 80° C.; and at a pressure in the range of from about 0.35 MPa to about 10 MPa, or from about 0.45 MPa to about 6 MPa, or from about 0.5 MPa to about 4 MPa.

In an embodiment, the run time of the reaction is from about 0.1 minutes to about 24 hours, or up to 16 hours, or in the range of from about 5 to 250 minutes, or from about 10 to 120 minutes.

In an embodiment, hydrogen is present in the polymerization reactor at a partial pressure of 0.001 to 50 psig (0.007 to 345 kPa), or from 0.01 to 25 psig (0.07 to 172 kPa), or 0.1 to 10 psig (0.7 to 70 kPa).

In an embodiment, the activity of the catalyst is at least 50 g/mmol/hour, or 500 or more g/mmol/hour, or 5000 or more g/mmol/hr, or 50,000 or more g/mmol/hr. In an alternate embodiment, the conversion of olefin monomer is at least 10%, based upon polymer yield and the weight of the monomer entering the reaction zone, or 20% or more, or 30% or more, or 50% or more, or 80% or more.

In an embodiment, the polymerization conditions include one or more of the following: 1) temperatures of 0 to 300° C. (or 25 to 150° C., or 40 to 120° C., or 45 to 80° C.); 2) a pressure of atmospheric pressure to 10 MPa (or 0.35 to 10 MPa, or 0.45 to 6 MPa, or from 0.5 to 4 MPa); 3) the presence of an aliphatic hydrocarbon solvent (such as isobutane, butane, pentane, isopentane, hexanes, isohexane, heptane, octane, dodecane, and mixtures thereof; cyclic and alicyclic hydrocarbons, such as, cyclohexane, cycloheptane, methylcyclohexane, methylcycloheptane, and mixtures thereof; or where aromatics are or present in the solvent at less than 1 wt %, or less than 0.5 wt %, or at 0 wt % based upon the weight of the solvents); and/or 4) optionally hydrogen is present in the polymerization reactor at a partial pressure of 0.007 to 345 kPa (0.001 to 50 psig) (or from 0.07 to 172 kPa (0.01 to 25 psig), or 0.7 to 70 kPa (0.1 to 10 psig)).

In an embodiment, the catalyst system used in the polymerization comprises no more than one catalyst compound. A "reaction zone" also referred to as a "polymerization zone," is a vessel where polymerization takes place, for example, a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In an embodiment, the polymerization occurs in one reaction zone.

Without limiting the above description, some processes described herein comprise:

contacting one or more olefins with a catalyst system described herein at a temperature, a pressure, and for a period of time sufficient to produce a polyolefin. In particular embodiments, the temperature is from about 0° C. to about 300° C., the pressure is from about 0.35 MPa to about 10 MPa, the time is from about 0.1 minutes to about 24 hours, or a combination thereof. Additionally or alternatively, the processes may be characterized by a temperature of from about 50° C. to about 150° C.

Polyolefin Products

The instant disclosure also relates to processes for using the catalyst systems described herein in olefin polymerization. Thus, the invention relates in part to processes for producing olefin polymers, e.g., polyethylene and polypropylene homopolymers and copolymers, particularly alpha-olefin copolymers. In an embodiment, the polymers produced herein are homopolymers of ethylene or propylene, are copolymers of ethylene having from 0 to 25 mol % (or from 0.5 to 20 mol %, or from 1 to 15 mol %, or from 3 to 10 mol %) of one or more $C_3$ to $C_{20}$ olefin comonomer (or $C_3$ to $C_{12}$ alpha-olefin, or propylene, butene, hexene, octene, decene, dodecene, or propylene, butene, hexene, octene), or are copolymers of propylene having from 0 to 25 mol % (or from 0.5 to 20 mol %, or from 1 to 15 mol %, or from 3 to 10 mol %) of one or more of $C_2$ or $C_4$ to $C_{20}$ olefin comonomer (or ethylene or $C_4$ to $C_{12}$ alpha-olefin, or ethylene, butene, hexene, octene, decene, dodecene, or ethylene, butene, hexene, octene).

In an embodiment, the monomer is ethylene and the comonomer is hexene, or from 1 to 15 mol % hexene, or 1 to 10 mol % hexene.

Polymers produced by the catalyst systems described herein typically have a Mw ≥about 5,000 g/mol, e.g., ≥about 10,000 g/mol, ≥about 25,000 g/mol, ≥about 50,000 g/mol, ≥about 75,000 g/mol, ≥about 100,000 g/mol, ≥about 125,000 g/mol, ≥about 150,000 g/mol, ≥about 200,000 g/mol, ≥about 225,000 g/mol, ≥about 250,000 g/mol, ≥about 300,000 g/mol, ≥about 325,000 g/mol, ≥about 350,000 g/mol, ≥about 500,000 g/mol, ≥about 750,000 g/mol, ≥about 1,000,000 g/mol, ≥about 1,250,000 g/mol, ≥about 1,500,000 g/mol, ≥about 1,750,000 g/mol, ≥about 2,000,000 g/mol, or ≥about 2,225,000 g/mol. Additionally or alternatively, the molecular weight may be ≤about 2,500,000 g/mol, e.g., ≤about 2,225,000 g/mol, ≤about 2,000,000 g/mol, ≤about 1,750,000 g/mol, ≤about 1,500,000 g/mol, ≤about 1,250,000 g/mol, ≤about 1,000,000 g/mol, ≤about 750,000 g/mol, ≤about 500,000 g/mol, ≤about 350,000 g/mol, ≤about 325,000 g/mol, ≤about 300,000 g/mol, ≤about 250,000 g/mol, ≤about 250,000 g/mol, ≤about 225,000 g/mol, ≤about 200,000 g/mol, ≤about 150,000 g/mol, ≤about 125,000 g/mol, ≤about 100,000 g/mol, ≤about 75,000 g/mol, ≤about 50,000 g/mol, ≤about 25,000 g/mol, or ≤about 10,000 g/mol. The molecular weight may be in a range formed by any of the above-enumerated values, e.g., about 5,000 to about 2,500,000 g/mol, about 10,000 to about 2,250,000 g/mol, about 25,000 to about 2,000,000 g/mol, about 50,000 to about 1,750,000 g/mol, about 75,000 to about 1,500,000 g/mol, about 100,000 to about 1,250,000 g/mol, etc. Additionally or alternatively, some polymers made with the catalyst systems described herein may have an Mw/Mn of greater than 1 to about 40, or 1.2 to 20, or 1.3 to 10, or 1.4 to 5, or 1.5 to 4, or 1.5 to 3.

In an embodiment, the polymer produced herein has a unimodal or multimodal molecular weight distribution as determined by Gel Permeation Chromotography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

In an embodiment, the polymers may be linear in character, which may be determined by elution fractionation, wherein non-linear polymers have a CDBI of less than 45%, whereas linear polyethylene types refer to polyethylene having a CDBI of greater than 50%, the CDBI being determined as described in WO 93/03093 (U.S. Pat. No. 5,206,075). In an embodiment, the polymer produced herein has a composition distribution breadth index (CDBI) of 50% or more, or 60% or more, or 70% or more. CDBI is a measure of the composition distribution of monomer within the polymer chains and is measured by the procedure described in WO 93/03093, published Feb. 18, 1993, specifically columns 7 and 8, as well as in Wild et al, J. Poly. Sci., Poly. Phys. Ed., Vol. 20, p. 441, (1982) and U.S. Pat. No. 5,008,204, including that fractions having a weight average molecular weight (Mw) below 15,000 are ignored when determining CDBI.

Polymers with an Mw/Mn of 4.5 or less may include a significant level of long chain branching. The long chain branching is understood to be the result of the incorporation of terminally unsaturated polymer chains (formed by the specific termination reaction mechanism encountered with single site catalysts) into other polymer chains in a manner analogous to monomer incorporation. The branches are hence believed to be linear in structure and may be present at a level where no peaks can be specifically attributed to such long chain branches in the $^{13}C$ NMR spectrum. In an embodiment, the polymers produced, according to the instant disclosure, comprise a significant amount of long chain branching, defined as having a ratio of long chain branching of at least 7 carbons per 1000 carbon atoms as determined according to the $^{13}C$ NMR spectrum of greater than 0.5. In an embodiment, the ratio of long chain branching with branches having at least 7 carbons, per 1000 carbon atoms as determined according to the $^{13}C$ NMR spectrum is greater than 1, or greater than 1.5, or greater than 2.

Polymers described herein may have one or more of the following features:

a) an Mn of at least 200 g/mol, measured by 1H NMR, or 250 g/mol to 100,000 g/mol, e.g., or 200 g/mol to 75,000 g/mol, e.g., or 200 g/mol to 60,000 g/mol, or 300 g/mol to 60,000 g/mol, or 750 g/mol to 30,000 g/mol); and/or b) a Tm, as determined by DSC, of 100° C. or more, or 110° C. or more, or 120° C. or more; and/or c) the polymer comprises at least 50 mol % ethylene, or at least 60 mol %, or at least 70 mol %, or at least 75 mol %, or at least 80 mol %, or at least 85 mol %, or at least 90 mol %, or at least 95 mol %, or essentially 100 mol % ethylene; and/or d) an Mw/Mn of greater than 1 to 4, or greater than 1 to 3.

In an embodiment, polymer produced herein has less than 1400 ppm aluminum, or less than 1200 ppm, or less than 1000 ppm, or less than 500 ppm, or less than 100 ppm as determined by ICPES (Inductively Coupled Plasma Emission Spectrometry), which is described in J. W. Olesik, "Inductively Coupled Plasma-Optical Emission Spectroscopy," in the Encyclopedia of Materials Characterization, C. R. Brundle, C. A. Evans, Jr. and S. Wilson, eds., Butterworth-Heinemann, Boston, Mass., 1992, pp. 633-644, which is used herein for purposes of determining the amount of an element in a material; and/or in an embodiment, the polymer has less than 1400 ppm of the Group 3, 4, 5, or 6 transition metal, or of the Group 4 transition metal, or of Ti, Zr, and/or Hf, or less than 1200 ppm, or less than 1000 ppm, or less than 500 ppm, or less than 100 ppm, as determined by ICPES as discussed above.

In an embodiment of the invention, an ethylene polymer, according to the instant disclosure, has less than 1400 ppm hafnium, or less than 1200 ppm, or less than 1000 ppm, or less than 500 ppm, or less than 100 ppm as determined by ICPES.

In an embodiment of the invention, an ethylene polymer, according to the instant disclosure, has less than 1400 ppm zirconium, or less than 1200 ppm, or less than 1000 ppm, or less than 500 ppm, or less than 100 ppm as determined by ICPES.

In an embodiment, the polymer produced herein, which may be an ethylene polymer, has a density of greater than 0.95 g/cc, or greater than 0.955 g/cc, or greater than 0.96 g/cc.

$^{13}$C NMR data is collected at 120° C. in a 10 mm probe using a Varian spectrometer with a $^1$Hydrogen frequency of at least 400 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra are acquired using time averaging to provide a signal to noise level adequate to measure the signals of interest. Samples are dissolved in tetrachloroethane-d$_2$ at concentrations between 10 to 15 wt % prior to being inserted into the spectrometer magnet. Prior to data analysis spectra are referenced by setting the chemical shift of the (—CH$_2$—)$_n$ signal where n>6 to 29.9 ppm. Chain ends for quantization are identified using the signals shown in the table below. N-butyl and n-propyl are not reported due to their low abundance (less than 5%) relative to the chain ends shown in the table below.

| Chain End | $^{13}$CNMR Chemical Shift |
|---|---|
| P~i-Bu | 23-5 to 25.5 and 25.8 to 26.3 ppm |
| E~i-Bu | 39.5 to 40.2 ppm |

-continued

| Chain End | $^{13}$CNMR Chemical Shift |
|---|---|
| P~Vinyl | 41.5 to 43 ppm |
| E~Vinyl | 33.9 to 34.4 ppm |

Polymer resonance peaks are referenced to mmmm=21.8 ppm. Calculations involved in the characterization of polymers by NMR are described by F. A. Bovey in Polymer Conformation and Configuration (Academic Press, New York 1969) and J. Randall in Polymer Sequence Determination, $^{13}$C-NMR Method (Academic Press, New York, 1977).

Differential Scanning Calorimetry (DSC)

Crystallization temperature ($T_c$), melting temperature (or melting point, $T_m$), glass transition temperature ($T_g$) and heat of fusion ($H_f$) are measured using Differential Scanning calorimetry (DSC) on a commercially available instrument (e.g., TA Instruments 2920 DSC). Typically, 6 to 10 mg of molded polymer or plasticized polymer are sealed in an aluminum pan and loaded into the instrument at room temperature. Data are acquired by heating the sample to at least 30° C. above its melting temperature, typically 220° C. for polypropylene, at a heating rate of 10° C./min. The sample is held for at least 5 minutes at this temperature to destroy its thermal history. Then the sample is cooled from the melt to at least 50° C. below the crystallization temperature, typically −100° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed according to standard procedures. The melting temperatures (Tm) reported are the peak melting temperatures from the second heat unless otherwise specified. For polymers displaying multiple peaks, the melting temperature is defined to be the peak melting temperature from the melting trace associated with the largest endothermic calorimetric response (as opposed to the peak occurring at the highest temperature). Likewise, the crystallization temperature is defined to be the peak crystallization temperature from the crystallization trace associated with the largest exothermic calorimetric response (as opposed to the peak occurring at the highest temperature).

Areas under the DSC curve are used to determine the heat of transition (heat of fusion, $H_f$, upon melting or heat of crystallization, $H_c$, upon crystallization), which can be used to calculate the degree of crystallinity (also called the percent crystallinity). The percent crystallinity (X %) is calculated using the formula: [area under the curve (in J/g)/H° (in J/g)]*100, where H° is the ideal heat of fusion for a perfect crystal of the homopolymer of the major monomer component. These values for H° are to be obtained from the Polymer Handbook, Fourth Edition, published by John Wiley and Sons, New York 1999, except that a value of 290 J/g is used for H° (polyethylene), a value of 140 J/g is used for H° (polybutene), and a value of 207 J/g is used for H° (polypropylene).

Heat of melting (Hm) is determined using the DSC procedure above except that the sample is cooled to −100° C., held for 5 minutes then heated at 10° C./min to 200° C. Hm is measured on the first melt, not the second melt. The Hm sample must have been aged at least 48 hours at room temperature and should not be heated to destroy thermal history.

Blends

In an embodiment, the polymer (e.g., the polyethylene or polypropylene) produced herein is combined with one or more additional polymers prior to being formed into a film, molded part, or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In an embodiment, the polymer (e.g., the polyethylene or polypropylene) is present in the above blends, at from 10 to 99 wt %, based upon the weight of the polymers in the blend, or 20 to 95 wt %, or at least 30 to 90 wt %, or at least 40 to 90 wt %, or at least 50 to 90 wt %, or at least 60 to 90 wt %, or at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX 1010 or IRGANOX 1076 available from Ciba-Geigy); phosphites (e.g., IRGAFOS 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

In an embodiment, the invention relates to polyolefins comprising ethylene, wherein the polyolefin is produced by a process comprising: contacting one or more olefins with a supported catalyst system as described herein at a temperature, a pressure, and for a period of time sufficient to produce a polyolefin. In some embodiments, the polyolefin comprises at least 50 mol %, e.g., at least 75 mol %, at least 99.9 mol % ethylene, of polymer units derived from ethylene.

Films

In an embodiment, any of the foregoing polymers, such as the foregoing polypropylenes or blends thereof, may be used in a variety of end-use applications. Applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxial orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the machine direction (MD) at a ratio of up to 15, or between 5 and 7, and in the transverse direction (TD) at a ratio of up to 15, or 7 to 9. However, in an embodiment, the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In an embodiment, one or more layers may be modified by corona treatment, electron beam irradiation, gamma irradiation, flame treatment, or microwave. In an embodiment, one or both of the surface layers is modified by corona treatment.

Molded Products

The compositions described herein (or polypropylene compositions) may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

Further, the compositions described herein (or polypropylene compositions) may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. Typically, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The tool stays closed to cool the film and the tool is then opened. The shaped laminate is then removed from the tool. The thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution.

Blow molding is another suitable forming means for use with the compositions of this invention, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or by calendaring. Sheets are generally considered to have a thickness of from 254 μm to 2540 μm (10 mils to 100 mils), although any given sheet may be substantially thicker.

Non-Wovens and Fibers

The polyolefin compositions described above may also be used to prepare nonwoven fabrics and fibers of this invention in any nonwoven fabric and fiber making process, including but not limited to, melt blowing, spinbonding, film aperturing, and staple fiber carding. A continuous filament process may also be used. Or a spunbonding process is used. The spunbonding process is well known in the art. Generally it involves the extrusion of fibers through a spinneret. These fibers are then drawn using high velocity air and laid on an endless belt. A calender roll is generally then used to heat the web and bond the fibers to one another although other techniques may be used such as sonic bonding and adhesive bonding.

Embodiments

Accordingly, the instant disclosure relates to the following embodiments:

1. A catalyst system comprising the result of the combination of and/or the reaction product of a fluorided support, an alumoxane activator, and a catalyst compound of Formula I:

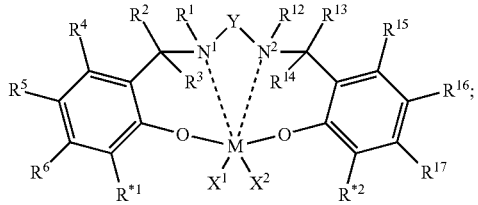

Formula I wherein:
each solid line represents a covalent bond and each dashed line represents a coordinative link;
wherein M is a Group 3, 4, 5, or 6 transition metal;
$N^1$ and $N^2$ are nitrogen;
O is oxygen;
each of $X^1$ and $X^2$ is, independently, a univalent $C_1$ to $C_{20}$ hydrocarbyl radical, a univalent $C_1$ to $C_{20}$ substituted hydrocarbyl radical (such as a functional group comprising elements from Groups 13 to 17 of the periodic table of the elements), or $X^1$ and $X^2$ join together to form a $C_4$ to $C_{62}$ cyclic or polycyclic ring structure, provided, however, when M is trivalent $X^2$ is not present;

each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), two or more of $R^1$, $R^2$, $R^3$, $R^4$, $R^5$, $R^6$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof;

wherein each of $R^{*1}$ and $R^{*2}$ independently comprises a bulky functional group, an electron withdrawing group, or a combination thereof; and Y is a divalent $C_1$ to $C_{20}$ hydrocarbyl radical.

2. The catalyst system of Embodiment 1, wherein the fluorided support comprises fluorided silica.

3. The catalyst system of Embodiment 2, wherein the fluorided silica has not been calcined at a temperature of 400° C. or more.

4. The catalyst system of any of Embodiments 1 to 3, wherein each of $R^{*1}$ and $R^{*2}$ independently comprises a cyclopentadienyl radical having a structure according to Formula II:

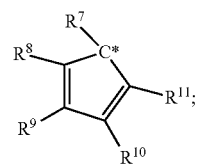

Formula II wherein:
C* indicates an attachment carbon of the radical;
$R^7$ is a $C_1$ to $C_{40}$ hydrocarbyl radical, a $C_1$ to $C_{40}$ substituted hydrocarbyl radical (such as a functional group comprising elements from Groups 13 to 17 of the periodic table of the elements); and
each of $R^8$, $R^9$, $R^{10}$, $R^{11}$ is, independently, hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof.

5. The catalyst system of any of Embodiments 1 to 4, wherein the catalyst compound has a structure according to Formula III:

Formula III

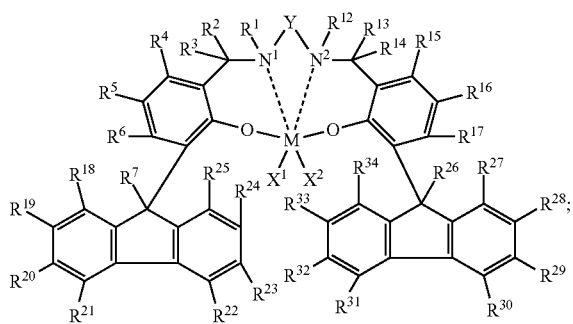

wherein:
each of $R^7$ and $R^{26}$ is, independently, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements);

wherein each of $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, and $R^{34}$ is, independently, hydrogen, a $C_1$ to $C_{40}$ hydrocarbyl radical is, a $C_1$ to $C_{40}$ substituted hydrocarbyl radical (such as a functional group comprising elements from Groups 13 to 17 of the periodic table of the elements), and wherein two or more of $R^1$, $R^2$, $R^3$, $R^4$, $R^5$, $R^6$, $R^7$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ may independently join together to form a $C_4$ to $C_{62}$ cyclic or polycyclic ring structure, or a combination thereof.

6. The catalyst system of Embodiment 5, wherein at least one of $R^5$ and/or $R^{16}$ is selected from the group consisting of $C_1$ to $C_{10}$ alkyl, $C_1$ to $C_{10}$ alkoxy, and $C_6$ to $C_{15}$ aryl.

7. The catalyst system of Embodiment 5, wherein each of $R^7$ and/or $R^{26}$ is selected from the group consisting of $C_1$ to $C_{10}$ alkyl groups, $C_1$ to $C_{10}$ alkoxy groups, $C_6$ to $C_{15}$ aryl groups, and combinations thereof.

8. The catalyst system of Embodiment 5, wherein each of $R^5$ and $R^{16}$ is independently selected from the group consisting of methyl, ethyl, n-propyl, i-propyl, n-butyl, sec-butyl, i-butyl, t-butyl, methoxy, ethoxy, n-propoxy, i-propoxy, n-butoxy, sec-butoxy, i-butoxy, t-butoxy, phenyl and $C_1$ to $C_5$ substituted phenyl groups;

wherein each of $R^7$ and $R^{26}$ is independently selected from the group consisting of ethyl, n-propyl, i-propyl, n-butyl, sec-butyl, i-butyl, t-butyl, phenyl, and $C_1$ to $C_5$ substituted phenyl groups;

wherein each of $R^1$, $R^2$, $R^3$, $R^4$, $R^6$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{27}$, $R^{28}$, $R^{29}$, $R^{30}$, $R^{31}$, $R^{32}$, $R^{33}$, and $R^{34}$ are each independently selected from H and $C_1$ to $C_5$ alkyl groups;

wherein Y is a divalent $C_1$ to $C_5$ hydrocarbyl radical, particularly —$(CH_2CH_2)$—; and wherein at least one of $X^1$ and/or $X^2$ is selected from $C_6$ to $C_{15}$ aryl groups, particularly benzyl.

9. The catalyst system of Embodiment 1, wherein each of $R^{*1}$ and $R^{*2}$ independently comprises a pyrrole radical having the structure according to Formula IV:

Formula IV

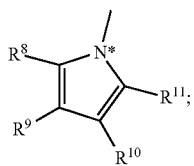

wherein:
N* indicates an attachment carbon of the radical; and
each of $R^8$, $R^9$, $R^{10}$, $R^{11}$ is, independently, hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), two or more of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure, or a combination thereof;

10. The catalyst system of Embodiment 1, wherein the catalyst compound has a structure according to Formula V:

Formula V

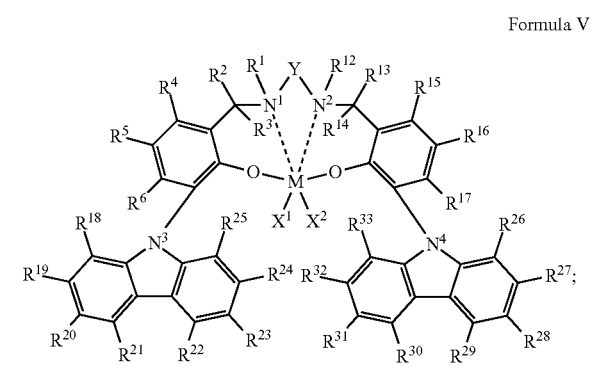

wherein:
each of $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ is, independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), or two or more of $R^1$ to $R^{33}$ may independently join together to form a $C_4$ to $C_{62}$ cyclic or polycyclic ring structure, or a combination thereof.

11. The catalyst system of Embodiment 10, wherein at least one of $R^5$ and/or $R^{16}$ is selected from the group consisting of $C_1$ to $C_{10}$ alkyl, $C_1$ to $C_{10}$ alkoxy, and $C_6$ to $C_{15}$ aryl.

12. The catalyst system of Embodiment 10, wherein each of $R^5$ and $R^{16}$ is independently selected from the group consisting of methyl, ethyl, n-propyl, i-propyl, n-butyl, sec-butyl, i-butyl, t-butyl, methoxy, ethoxy, n-propoxy, i-propoxy, n-butoxy, sec-butoxy, i-butoxy, t-butoxy, phenyl, and $C_1$-$C_5$ substituted phenyl groups;

wherein each of $R^1$, $R^2$, $R^3$, $R^4$, $R^6$, $R^{12}$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ are each independently selected from H and $C_1$ to $C_5$ alkyl groups;

wherein Y is a divalent $C_1$ to $C_5$ hydrocarbyl radical, particularly —$(CH_2CH_2)$—; and wherein at least one of $X^1$ and/or $X^2$ is selected from the group consisting of a halogen or a $C_1$ to $C_7$ hydrocarbyl radical, and a $C_6$ to $C_{15}$ aryl group, particularly benzyl.

13. The catalyst compound of Embodiment 10, wherein Y is a $C_1$-$C_{40}$ divalent hydrocarbyl radical comprising O, S, S(O), S(O)$_2$, Si(R')$_2$, P(R'), N, N(R'), or a combination thereof, wherein each R' is independently a $C_1$-$C_{18}$ hydrocarbyl radical.

14. The catalyst compound of Embodiment 10, wherein:
M is Zr;
$X^1$ and $X^2$ are benzyl radicals;
$R^1$ and $R^{12}$ are methyl radicals;
$R^2$, $R^3$, $R^4$, $R^5$, $R^6$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, and $R^{25}$ are hydrogen;
$R^{16}$ is bromine; and
Y is —CH$_2$CH$_2$—.

15. The catalyst compound of Embodiment 10, wherein:
M is Zr;
$X^1$ and $X^2$ are benzyl radicals;
$R^1$, $R^{12}$ and $R^{16}$ are methyl radicals;
$R^2$, $R^3$, $R^4$, $R^5$, $R^6$, $R^{13}$, $R^{14}$, $R^{15}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ $R^{32}$, and $R^{33}$ are hydrogen; and
Y is —CH$_2$CH$_2$—.

16. The catalyst system of Embodiment 1, wherein the catalyst compound has a structure according to Formula VI:

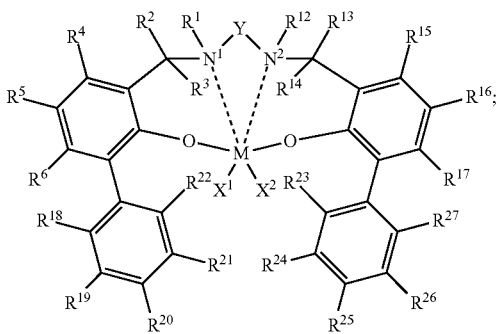

Formula VI wherein:
each of $R^{18}$, $R^{19}$, $R^{20}$, $R^{21}$, $R^{22}$, $R^{23}$, $R^{24}$, $R^{25}$, $R^{26}$, and $R^{27}$ is, independently, a hydrogen, a $C_1$ to $C_{40}$ hydrocarbyl radical, a functional group comprising elements from Groups 13 to 17 of the periodic table of the elements, or two or more of $R^1$ to $R^{33}$ may independently join together to form a $C_4$ to $C_{62}$ cyclic or polycyclic ring structure, or a combination thereof.

17. The catalyst system of Embodiment 16, wherein Y is a divalent $C_1$ to $C_5$ hydrocarbyl radical, particularly —(CH$_2$CH$_2$)—; and wherein at least one of $X^1$ and/or $X^2$ is selected from the group consisting of a halogen or a $C_1$ to $C_7$ hydrocarbyl radical, and a $C_6$ to $C_{15}$ aryl group, particularly benzyl.

18. The catalyst system of Embodiment 16, wherein M is Hf, Ti, or Zr.

19. The catalyst system of Embodiment 16, wherein each of $X^1$ and $X^2$ is, independently, a halogen or a $C_1$ to $C_7$ hydrocarbyl radical.

20. The catalyst system of Embodiment 16, wherein each of $X^1$ and $X^2$ is a benzyl radical.

21. The catalyst system of Embodiment 16, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, hydrogen, a halogen, or a $C_1$ to $C_{30}$ hydrocarbyl radical.

22. The catalyst compound of Embodiment 16, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, hydrogen, a halogen, or a $C_1$ to $C_{10}$ hydrocarbyl radical.

23. The catalyst system of Embodiment 16, wherein one or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is a methyl radical, a fluoride, or a combination thereof.

24. The catalyst system of Embodiment 16, wherein Y is —CH$_2$CH$_2$— or 1,2-cyclohexylene.

25. The catalyst system of Embodiment 16, wherein Y is —CH$_2$CH$_2$CH$_2$—.

26. The catalyst system of Embodiment 16, wherein Y is a $C_1$ to $C_{40}$ divalent hydrocarbyl radical comprising a linker backbone comprising from 1 to 18 carbon atoms bridging between nitrogen atoms $N^1$ and $N^2$.

27. The catalyst system of Embodiment 16, wherein Y is a $C_1$ to $C_{40}$ divalent hydrocarbyl radical comprising O, S, S(O), S(O)$_2$, Si(R')$_2$, P(R'), N, N(R'), or a combination thereof, wherein each R' is independently a $C_1$ to $C_{18}$ hydrocarbyl radical.

28. The catalyst system of Embodiment 16, wherein:
M is Ti;
$X^1$ and $X^2$ are benzyl radicals;
$R^1$ and $R^{12}$ are methyl radicals;
$R^2$, $R^3$, $R^4$, $R^6$, $R^{13}$, $R^{14}$, $R^{15}$, $R^{16}$ and $R^{17}$ are hydrogen;
$R^5$, $R^{16}$, $R^{18}$, $R^{19}$, $R^{20}$, $R^{21}$, $R^{22}$, $R^{23}$, $R^{24}$, $R^{25}$, $R^{26}$, and $R^{27}$ are fluorine; and
Y is —CH$_2$CH$_2$—.

29. The catalyst system of Embodiment 16, wherein:
M is Ti;
$X^1$ and $X^2$ are benzyl radicals;
$R^1$, $R^5$, $R^{12}$, and $R^{16}$ are methyl radicals;
$R^2$, $R^3$, $R^4$, $R^6$, $R^{13}$, $R^{14}$, $R^{15}$, and $R^{17}$ are hydrogen;
$R^{18}$, $R^{19}$, $R^{20}$, $R^{21}$, $R^{22}$, $R^{23}$, $R^{24}$, $R^{25}$, $R^{26}$, and $R^{27}$ are fluorine; and
Y is —CH$_2$CH$_2$—.

30. The catalyst compound of Embodiment 16, wherein:
M is Zr;
$X^1$ and $X^2$ are benzyl radicals;
$R^1$ and $R^{12}$ are methyl radicals;
$R^2$, $R^3$, $R^4$, $R^6$, $R^{13}$, $R^{14}$, $R^{15}$, and $R^{17}$ are hydrogen;
$R^5$, $R^{16}$, $R^{18}$, $R^{19}$, $R^{20}$, $R^{21}$, $R^{22}$, $R^{23}$, $R^{24}$, $R^{25}$, $R^{26}$, and $R^{27}$ are fluorine; and
Y is —CH$_2$CH$_2$—.

31. The catalyst compound of Embodiment 16, wherein:
M is Zr;
$X^1$ and $X^2$ are benzyl radicals;
$R^1$, $R^5$, $R^{12}$, and $R^{16}$ are methyl radicals;
$R^2$, $R^3$, $R^4$, $R^6$, $R^{12}$, $R^{14}$, $R^{15}$, and $R^{17}$ are hydrogen;
$R^{18}$, $R^{19}$, $R^{20}$, $R^{21}$, $R^{22}$, $R^{23}$, $R^{24}$, $R^{25}$, $R^{26}$, and $R^{27}$ (are fluorine; and
Y is —CH$_2$CH$_2$—.

32. The catalyst system of Embodiment 1, wherein the catalyst compound has a structure according to Formula VII:

Formula VII

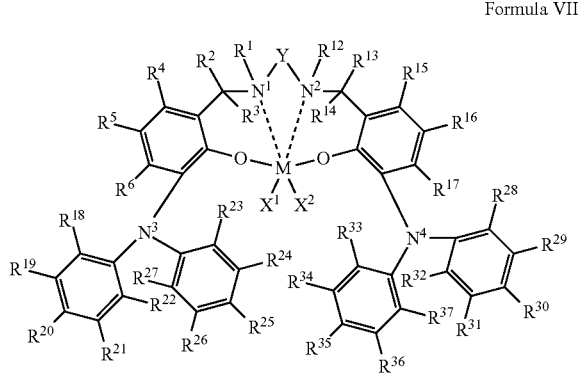

wherein:
each solid line represents a covalent bond and each dashed line represents a coordinative link;
M is a Group 3, 4, 5, or 6 transition metal;
$N^1$, $N^2$, $N^3$, and $N^4$ are nitrogen;
O is oxygen;
each of $X^1$ and $X^2$ is, independently, a univalent $C_1$ to $C_{20}$ hydrocarbyl radical, a univalent substituted $C_1$ to $C_{20}$ hydrocarbyl radical (such as a functional group comprising elements from Groups 13 to 17 of the periodic table of the elements, or $X^1$ and $X^2$ join together to form a $C_4$ to $C_{62}$ cyclic or polycyclic ring structure, provided, however, when M is trivalent $X^2$ is not present;
Y is a divalent hydrocarbyl radical covalently bonded to and bridging between both of the nitrogen atoms $N^1$ and $N^2$; and
each of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$ and $R^{37}$, and is independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), or two or more of $R^1$ to $R^{32}$ may independently join together to form a $C_4$ to $C_{62}$ cyclic or polycyclic ring structure wherein neither $R^{18}$ and $R^{22}$ join together with $R^{23}$ or $R^{27}$ to form direct covalent bonds between the respective aromatic rings and wherein neither $R^{33}$ and $R^{37}$ join together with $R^{28}$ or $R^{32}$ to form direct covalent bonds between the respective aromatic rings, or a combination thereof.

33. The catalyst system of Embodiment 32, wherein M is Hf, Ti, or Zr.

34. The catalyst compound of Embodiment 30, wherein each of $X^1$ and $X^2$ is, independently, a halogen or a $C_1$ to $C_7$ hydrocarbyl radical.

35. The catalyst system of Embodiment 32, wherein each of $X^1$ and $X^2$ is a benzyl radical.

36. The catalyst system of Embodiment 32, wherein Y is —$CH_2CH_2$— or 1,2-cyclohexylene.

37. The catalyst system of Embodiment 32, wherein Y is —$CH_2CH_2CH_2$—.

38. The catalyst system of Embodiment 32, wherein Y is a $C_1$ to $C_{40}$ divalent hydrocarbyl radical comprising a linker backbone comprising from 1 to 18 carbon atoms bridging between nitrogen atoms $N^1$ and $N^2$.

39. The catalyst system of Embodiment 32, wherein Y is a $C_1$ to $C_{40}$ divalent hydrocarbyl radical comprising O, S, S(O), S(O)$_2$, Si(R')$_2$, P(R'), N, N(R'), or a combination thereof, wherein each R' is independently a $C_1$ to $C_{18}$ hydrocarbyl radical.

40. The catalyst system of Embodiment 30, wherein each of $R^1$, $R^2$, $R^3$, $R^4$, $R^5$, $R^6$, $R^{12}$, $R^{13}$, $R^{14}$, $R^{15}$, $R^{16}$, $R^{17}$, $R^{19}$, $R^{20}$, $R^{21}$, $R^{24}$, $R^{25}$, $R^{26}$, $R^{29}$, $R^{30}$, $R^{31}$, $R^{34}$, $R^{35}$, and $R^{36}$ is, independently, a hydrogen, a $C_1$ to $C_{40}$ hydrocarbyl radical, a functional group comprising elements from Groups 13 to 17 of the periodic table of the elements, or two or more of $R^1$, $R^2$, $R^3$, $R^4$, $R^5$, $R^6$, $R^{12}$, $R^{13}$, $R^{14}$, $R^{15}$, $R^{16}$, $R^{17}$, $R^{19}$, $R^{20}$, $R^{21}$, $R^{24}$, $R^{25}$, $R^{26}$, $R^{29}$, $R^{30}$, $R^{31}$, $R^{34}$, $R^{35}$, and $R^{36}$ may independently join together to form a $C_4$ to $C_{62}$ cyclic or polycyclic ring structure, or a combination thereof; and each $R^{18}$, $R^{22}$, $R^{23}$, $R^{27}$, $R^{28}$, $R^{32}$, $R^{33}$, and $R^{37}$ and is, independently, a hydrogen, a $C_1$ to $C_{40}$ hydrocarbyl radical, a functional group comprising elements from Groups 13 to 17 of the periodic table of the elements, or a combination thereof.

41. The catalyst system of Embodiment 32, wherein each of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ is, independently, hydrogen, a halogen, or a $C_1$ to $C_{30}$ hydrocarbyl radical.

42. The catalyst system of Embodiment 32, wherein each of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ is, independently, hydrogen, a halogen, or a $C_1$ to $C_{10}$ hydrocarbyl radical.

43. The catalyst system of Embodiment 32, wherein one or more of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ is a methyl radical, a fluoride, or a combination thereof.

44. The catalyst system of Embodiment 32, wherein $R^{22}$ and $R^{27}$ join together to form a divalent $C_1$ to $C_{20}$ hydrocarbyl radical, a divalent functional group comprising elements from Groups 13 to 16 of the periodic table of the elements, or a combination thereof, and wherein $R^{32}$ and $R^{37}$ join together to form a divalent $C_1$ to $C_{20}$ hydrocarbyl radical, a divalent functional group comprising elements from Groups 13 to 16 of the periodic table of the elements, or a combination thereof.

45. The catalyst system of Embodiment 32, wherein:
M is Zr;
$X^1$ and $X^2$ are benzyl radicals;
$R^1$ and $R^{12}$ are methyl radicals;
$R^2$, $R^3$, $R^4$, $R^5$, $R^6$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ are hydrogen; and
Y is —$CH_2CH_2$—.

46. The catalyst system of Embodiment 32, wherein:
M is Zr;
$X^1$ and $X^2$ are benzyl radicals;
$R^1$, $R^5$, $R^{12}$, and $R^{16}$ are methyl radicals;
$R^2$, $R^3$, $R^4$, $R^6$, $R^{13}$, $R^{14}$, $R^{15}$, $R^{17}$, to $R^{37}$ are hydrogen; and
Y is —$CH_2CH_2$—.

47. The catalyst system of Embodiment 1, wherein the catalyst compounds is represented by Formula VIII:

Formula VIII

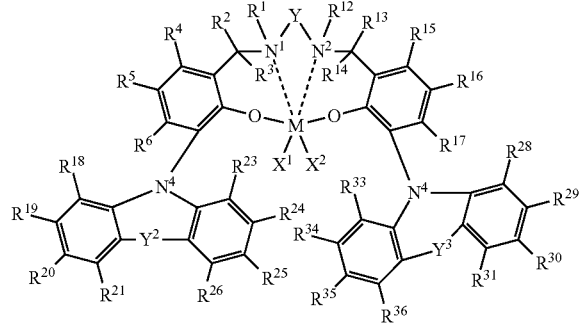

wherein:

each solid line represents a covalent bond and each dashed line represents a coordinative link;

M is a Group 3, 4, 5, or 6 transition metal;

$N^1$, $N^2$, $N^3$, and $N^4$ are nitrogen;

O is oxygen;

each of $X^1$ and $X^2$ is, independently, a univalent $C_1$ to $C_{20}$ hydrocarbyl radical, a $C_1$ to $C_{20}$ substituted hydrocarbyl radical (such as a functional group comprising elements from Groups 13 to 17 of the periodic table of the elements), or $X^1$ and $X^2$ join together to form a $C_4$ to $C_{62}$ cyclic or polycyclic ring structure, provided however when M is trivalent $X^2$ is not present;

Y is a divalent $C_1$ to $C_{20}$ hydrocarbyl radical;

$Y^2$ and $Y^3$ are independently a divalent $C_1$ to $C_{20}$ hydrocarbyl radical, a $C_1$ to $C_{20}$ substituted hydrocarbyl radical (such as a divalent functional group comprising elements from Groups 13 to 16 of the periodic table of the elements), or a combination thereof; and each $R^1$ to $R^6$, $R^{12}$ to $R^{21}$, $R^{23}$ to $R^{26}$, $R^{28}$ to $R^{31}$, and $R^{33}$ to $R^{36}$ is, independently, a hydrogen, a $C_1$ to $C_{40}$ hydrocarbyl radical, a $C_1$ to $C_{40}$ substituted hydrocarbyl radical (such as a functional group comprising elements from Groups 13 to 17 of the periodic table of the elements), or two or more of $R^1$ to $R^6$, $R^{12}$ to $R^{21}$, $R^{23}$ to $R^{26}$, $R^{28}$ to $R^{31}$, and $R^{33}$ to $R^{36}$ may independently join together to form a $C_4$ to $C_{62}$ cyclic or polycyclic ring structure.

48. A process comprising:

contacting one or more olefins with a catalyst system of any of Embodiments 1 to 46 at a temperature, a pressure, and for a period of time sufficient to produce a polyolefin.

49. The process of Embodiment 48, wherein the temperature is from about 0° C. to about 300° C., the pressure is from about 0.35 MPa to about 10 MPa, the time is from about 0.1 minutes to about 24 hours, or a combination thereof.

50. The process of Embodiment 48 or 49, wherein the temperature is from about 50° C. to about 150° C.

51. A polyolefin comprising ethylene, wherein the polyolefin is produced by a process comprising:

contacting ethylene and or more comonomers with a catalyst system of any of Embodiments 1 to 50 at a temperature, a pressure, and for a period of time sufficient to produce a polyolefin.

52. The polyolefin of Embodiment 51, wherein the polyolefin comprises at least 50 mol % of polymer units derived from ethylene.

53. The polyolefin of Embodiment 51, wherein the polyolefin comprises at least 75 mol % of polymer units derived from ethylene.

54. The polyolefin of Embodiment 51, wherein the polyolefin comprises at least 99.9 mol % of polymer units derived from ethylene.

55. The polyolefin of Embodiment 51, wherein the polyolefin has an Mn of 250 g/mol to 2,500,000 g/mol.

56. The polyolefin of Embodiment 51, wherein hexene comonomer is present at 0.1 to <50 mol %.

Experimental

Melt index (MI) also referred to as $I_2$, reported in g/10 min, is determined according to ASTM D1238, 190° C., 2.16 kg load.

High load melt index (HLMI) also referred to as $I_{21}$, reported in g/10 min, is determined according to ASTM D1238, 190° C., 21.6 kg load.

Melt index ratio (MIR) is MI divided by HLMI as determined by ASTM D1238.

Density is determined according to ASTM D1505.

Bulk Density is measured according to ASTM D1895.

Mw, Mn, and Mz, may be determined by Rapid GPC and percent of 1-hexene incorporation may be determined by FT-IR to determine various molecular weight related values by GPC, high temperature size exclusion chromatography is performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is incorporated herein by reference for US purposes. This apparatus has a series of three 30 cm*7.5 mm linear columns, each containing PLgel 10 μm, Mix B. The GPC system is calibrated using polystyrene standards ranging from 580-3,390,000 g/mol. The system is operated at an eluent flow rate of 2.0 mL/minutes and an oven temperature of 165° C. 1,2,4-trichlorobenzene was used as the eluent. The polymer samples are dissolved in 1,2,4-trichlorobenzene at a concentration of 0.1-0.9 mg/mL. 250 uL of a polymer solution is injected into the system. The concentration of the polymer in the eluent is monitored using an evaporative light scattering detector. The molecular weights presented are relative to linear polystyrene standards and are uncorrected.

EXAMPLES

The foregoing discussion can be further described with reference to the following non-limiting examples. Illustrative catalyst compounds (A-H), each according to one or more embodiments described, are synthesized and some are used to polymerize olefins. All reactions are carried out under a purified nitrogen atmosphere using standard glovebox, high vacuum, or Schlenk techniques, unless otherwise noted. All solvents used are anhydrous, de-oxygenated, and purified according to known procedures. All starting materials are either purchased from Aldrich and purified prior to use or prepared according to procedures known to those skilled in the art.

Synthesis of Compound A

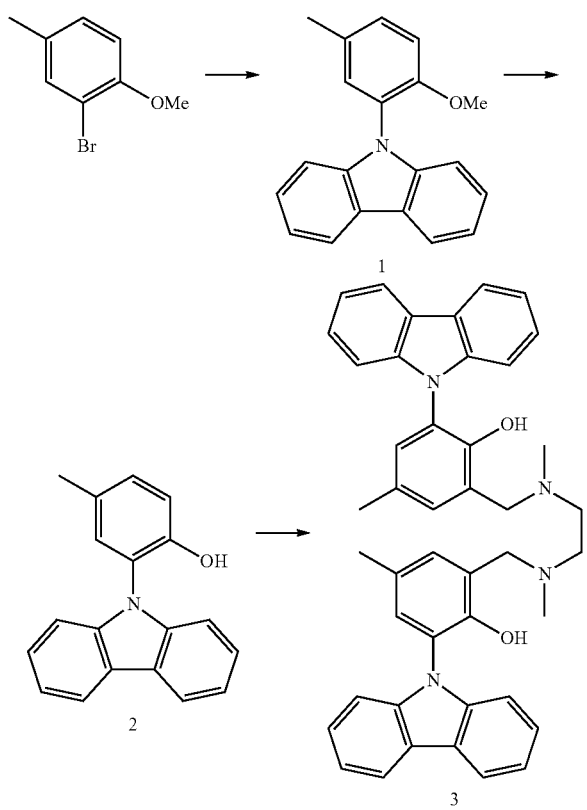

9-(2-Methoxy-5-methylphenyl)-9H-carbazole (1)

2-Bromo-4-methylanisole (20.11 g, 100 mmol, 1 equiv) and carbazole (20.06 g, 120 mmol, 1.2 equiv) are dissolved in 1,4-dioxane (400 mL). Potassium phosphate tribasic (37.15 g, 175 mmol, 1.75 equiv), copper (I) iodide (0.95 g, 5 mmol, 0.05 equiv) and racemic trans-1,2-diaminocyclohexane (2.4 mL, 20 mmol, 0.2 equiv) are added and the reaction is refluxed for two days. The reaction is cooled to room temperature, then partitioned with ethyl acetate (200 mL) and water (300 mL). The aqueous layer is extracted with ethyl acetate (3×200 mL). The combined organic layers are washed with saturated brine, dried over sodium sulfate, filtered, and concentrated under reduced pressure. The residue is purified over silica gel (150 g), eluting with 3% ethyl acetate in heptanes to give compound 1 (13.5 g, 45% yield) as a yellow solid.

2-(9H-Carbazol-9-yl)-4-methylphenol (2)

A 1.0 M boron tribromide solution in dichloromethane (90 mL, 90 mmol, 1.9 equiv) is added dropwise at −78° C., over 30 minutes, to a solution of compound 1 (13.5 g, 46.98 mmol, 1 equiv) in anhydrous dichloromethane (400 mL). The reaction is warmed to room temperature, when liquid chromatography/mass spectrometry (LCMS) indicated that the reaction is complete. The reaction is quenched with ice-water (200 mL). The layers are separated and the aqueous phase is extracted with dichloromethane (2×100 mL). The combined organic layers are dried over sodium sulfate, filtered, and concentrated under reduced pressure. The residue is purified on an ANALOGIX 40-150 g column, eluting with a gradient of 0 to 20% ethyl acetate in heptanes to give compound 2 (12.3 g, 95% yield) as a yellow oil.

6,6'-((Ethane-1,2-diylbis(methylazanediyl))bis(methylene))bis(2-(9H-carbazol-9-yl)-4-methylphenol) (3)

A mixture of compound 2 (3.4 g, 12.44 mmol, 2 equiv), paraformaldehyde (1.87 g, 62.2 mmol, 10 equiv), N,N'-dimethylethylenediamine (0.67 mL, 6.22 mmol, 1 equiv) and anhydrous ethanol (100 mL) is refluxed for 18 hours. The reaction is cooled to room temperature, and then concentrated under reduced pressure. The residue is purified on an ANALOGIX 25-60 g column, eluting with a gradient of 0 to 30% ethyl acetate in heptanes to give compound 3 (1.1 g, 27% yield) as a white solid.

In a nitrogen purged glovebox, the ligand (3) is dissolved in toluene in a scintillation vial. In a separate vial, 1 equivalent of zirconium tetrabenzyl is also dissolved in toluene. The solution of ligand 3 is stirred and the tetrabenzyl solution is added dropwise. After stirring for one hour, the solution is filtered with a syringe adapted with a 0.2 micron filter tip. The toluene is then removed under nitrogen and the resulting residue is slurried in pentane. Solids are collected using a frit, dried under vacuum and analyzed by $^1$H NMR spectroscopy.

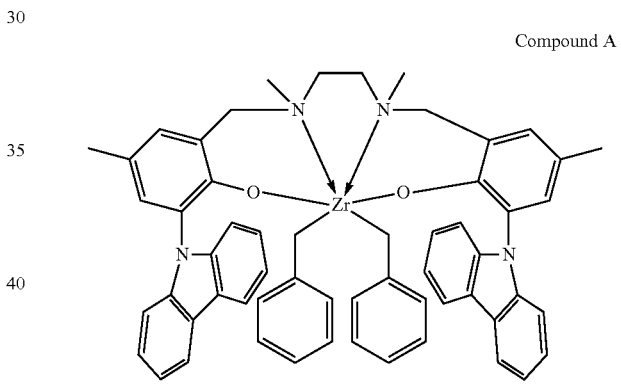

Compound A

Synthesis of Compound B

Compound B is prepared as described above for Compound A using Hf(Bn)$_4$ in place of Zr(Bn)$_4$.

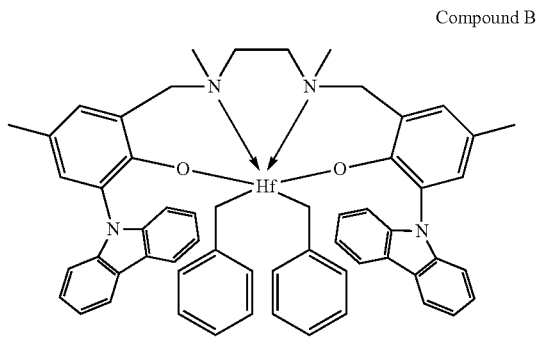

Compound B

Synthesis of Compound C

Synthesis of 9-methy-9H-fluoren-9-ol (1)

In a glovebox, in a 50 mL round bottom flask, 9H-fluorene-9-one (5.458 g, 30.3 mmol) is dissolved in 20 mL of THF and cooled to 0° C. for 30 minutes. MeMgBr (1.2 eq.) is then slowly added via syringe while stirring. A slurry formed once all of the Grignard is added. The reaction is allowed to stir for 48 hours. The flask is then removed from the glovebox and 4 mL of 2M NaOH are added. The mixture is washed with brine and the organic portion collected and dried over $MgSO_4$, filtered, and the volatiles removed under a $N_2$ stream. NMR of the resultant yellow solid showed pure 9-methyl-9H-fluoren-9-ol. Yield is 5.67 g (95 wt %).

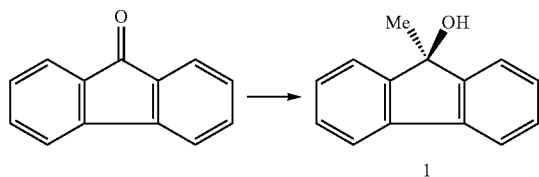

Synthesis of 4-methyl-2-(9-methyl-9H-fluoren-9-yl)phenol (2)

In a 200 mL round bottom flask, p-cresol (2.075 g, 19.2 mmol) and 2 (3.766 g, 19.2 mmol) are dissolved in 80 mL of $CH_2Cl_2$. 4 mL of conc. $H_2SO_4$ (5 eq.) are added dropwise to the solution while stirring to produce a dark purple solution. After two hours, the purple solution is added slowly to 100 mL of $H_2O$ forming a white/blue precipitate. 2M NaOH is then added dropwise until the pH reached 9-10. The slurry is then washed with $CH_2Cl_2$ (3×100 mL). The organic portion is then collected and dried with $MgSO_4$. Volatiles are removed under $N_2$ leaving a brownish residue. The resultant product is purified on a silica column using a 5-10% gradient of EtOAc/Hexane.

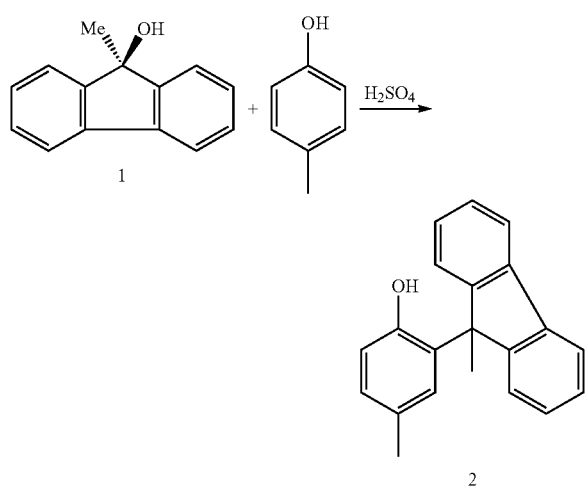

Synthesis of 6,6'-(ethane-1,2-diylbis(methyl-azanediyl)) bis(methylene)bis)4-methyl-2-(9-methyl-9H-fluoren-9-yl)phenol (3)

In a 100 mL round bottom flask, 2 (0.512 g, 1.8 mmol), $N^1,N^2$-dimethylethane-1,2-diamine (0.079 g, 0.9 mmol) and formaldehyde (0.268 g, 8.9 mmol) are dissolved in 30 mL of ethanol. The flask is placed in an oil bath and heated to reflux for 16 hours. The ethanol is removed under a $N_2$ stream to give a yellow oil. The product is purified on a silica column using $CH_2Cl_2$/hexane.

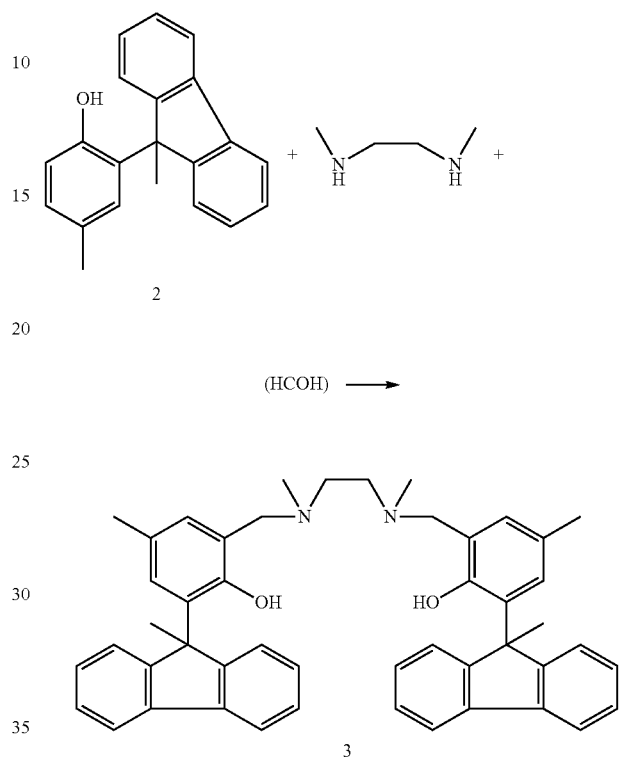

Synthesis of [6,6'-(ethane-1,2-diylbis(methyl-azanediyl)) bis(methylene)bis)4-methyl-2-(9-methyl-9H-fluoren-9-yl)phenolate]zirconium(IV) dibenzyl (4)

In a vial, 3 (0.152 g. 0.22 mmol) is dissolved in 5 mL of toluene. In a separate vial, $Zr(Bn)_4$ (0.101 g, 0.22 mmol) is dissolved in 5 mL of toluene. The zirconium solution is added to the ligand solution while stirring and allowed to stir for 1 h. Toluene is then removed resulting in a yellow/orange residue. The residue is slurried in pentane, then filtered leaving a yellow solid and orange filtrate. Yield of yellow solid (4) is 0.153 g (73 wt %).

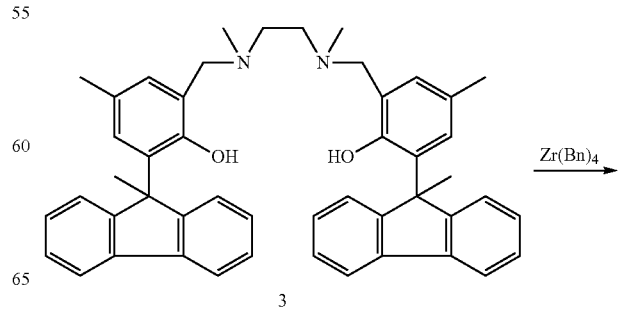

-continued

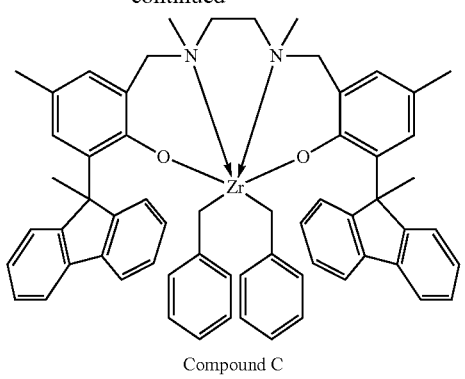

Compound C

Synthesis of Compound D

Compound D is prepared as described above for Compound C using Hf(Bn)₄ in place of Zr(Bn)₄.

Compound D

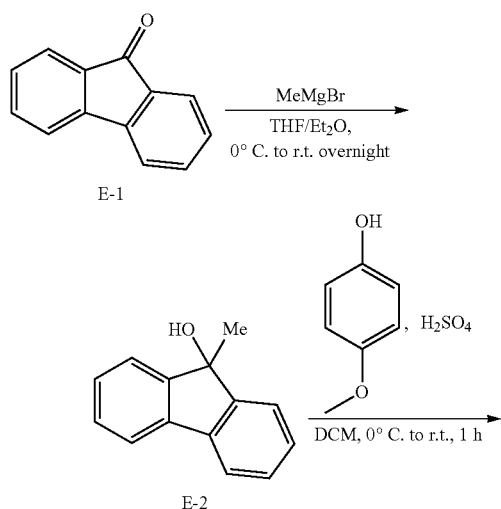

Synthesis of Compound E

Scheme 2: Synthesis of Ligand E

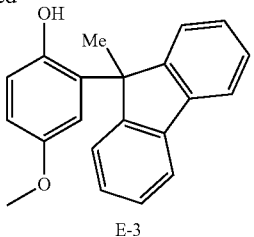

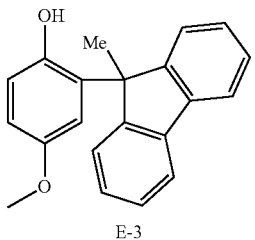

E-3

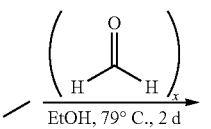

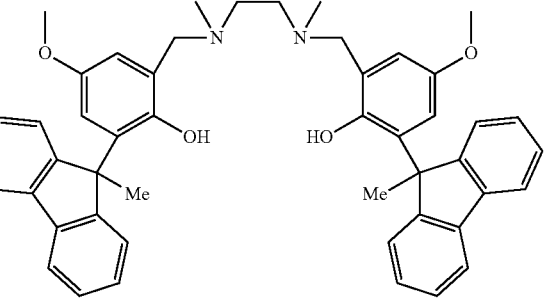

E

E-2: In a glove-box at −30° C., E-1, fluorenone, (10.00 g, 55.5 mmol) in tetrahydrofuran (25 mL), is added to methylmagnesium bromide (22.2 mL, 66.6 mmol) in diethyl ether (150 mL). The reaction solution is stirred at r.t. overnight. The reaction solution is cooled to 0° C. and 150 mL of water is added. The solution is brought to a pH of 9 with 2M NaOH. Organics are extracted with diethyl ether (3×100 mL), dried with magnesium sulfate, filtered and concentrated in vacuo yielding the yellow oil, E-2 (8.81 g, 144.89 mmol, 80.7% yield).

E-3: In a hood, E-2 (8.63 g, 43.98 mmol) in dichloromethane (250 mL) is added drop-wise (over about 20 min) with an addition funnel to a solution of 4-methoxyphenol (10.919 g, 87.96 mmol) and sulfuric acid (3.0 mL, 46.18 mmol) in dichloromethane (250 mL) at 0° C. The solution is stirred at room temperature for 1 h. The reaction mixture is poured into water (200 mL) and brought to a pH>7 (2M sodium hydroxide). Organic layer is washed with brine (4×250 mL), dried with magnesium sulfate, filtered, and concentrated in vacuo. The product is purified via column chromatography (20-50% DCM/hexane followed by 10-40% Ethyl acetate/hexane). This gave compound E-3 (9.75 g, 29.69 mmol, 667.50% yield) as a white solid.

F: In a dry-box, at room temperature, paraformaldehyde (0.892 g, 29.69 mmol) then N,N'-dimethylethylenediamine (1.31 g, 1.6 mL, 14.845 mmol) are added to F-3 (9.75 g, 29.69 mmol) in ethanol (33 mL). The reaction solution is stirred for 3 days at 80° C. The reaction solution is cooled to room temperature and the solvent is removed in vacuo yielding desired product, F (10.12 g, 14.116 mmol, 95.09% yield).

In a nitrogen purged glovebox, the ligand F is dissolved in toluene in a scintillation vial. In a separate vial, 1 equivalent of zirconium tetrabenzyl is also dissolved in toluene. The solution of ligand 3 is stirred and the tetrabenzyl solution is added dropwise. After stirring for one hour, the solution is filtered with a syringe adapted with a 0.2 micron filter tip. The toluene is then removed under nitrogen and the resulting residue is slurried in pentane. Solids are collected using a frit, dried under vacuum, and analyzed by $^1$H NMR spectroscopy.

Compound E

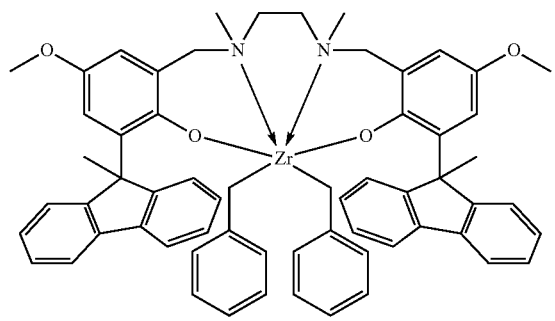

Synthesis of Compound F

Compound F is prepared as described above for Compound E using Hf(Bn)$_4$ in place of Zr(Bn)$_4$.

Compound F

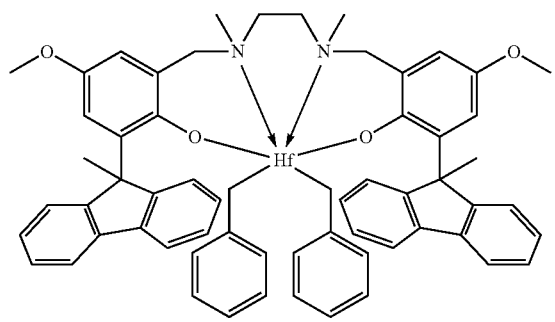

Synthesis of Compound G

Scheme 1: Synthesis of Ligand G

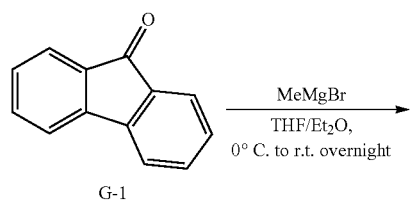

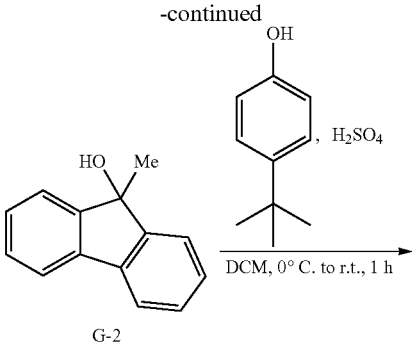

G-2

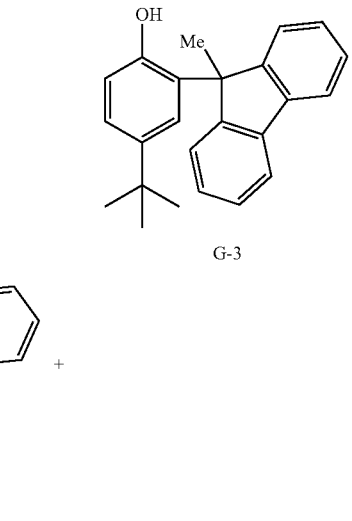

G-3

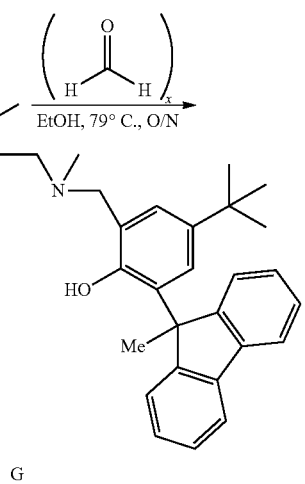

G

G-2: In the glove-box at 0° C., G-1, fluorenone, (30.00 g, 166.5 mmol) in tetrahydrofuran (70 mL) is added to methylmagnesium bromide (66.5 mL, 199.5 mmol) in diethyl ether (500 mL). The reaction solution is stirred at r.t. overnight. The reaction solution is cooled to 0° C. and 200 mL of water is added. The solution is brought to a pH of 9 with 2M NaOH. The organic fraction is washed with brine (3×200 mL), dried with magnesium sulfate, filtered and concentrated in vacuo yielding the yellow oil, G-2 (29.10 g, 148.28 mmol, 89.06% yield).

G-3: In the hood, G-2 (229.10 g, 148.28 mmol) in dichloromethane (400 mL) is added drop-wise (over about 20 min) with an addition funnel to a solution of 4-tert-butylphenol (22.28 g, 148.28 mmol) and sulfuric acid (8.65 mL, 155.69 mmol) in dichloromethane (300 mL) at 0° C. The solution is stirred at room temperature for 1 h. The reaction mixture is poured into water (300 mL) and brought to a pH of 9 (2M sodium hydroxide). Organic layer is washed with brine (4×250 mL), dried with magnesium sulfate, filtered, and concentrated in vacuo. This gave compound G-3 (44.23 g, 134.66 mmol, 90.82% yield) as a white solid.

G: In the dry-box, at room temperature, paraformaldehyde (5.6 g, 186.0 mmol) then N,N'-dimethylethylenediamine (8.20 g, 10.0 mL, 93.1 mmol) are added to G-3 (61.09 g, 186.0 mmol) in ethanol (550 mL). Note: multiple batches of G-3 are combined to synthesize G. The reaction solution is stirred 3 days at 80° C. The reaction solution is cooled to room temperature and the solvent is removed in vacuo yielding desired product, G (60.044 g, 81.0 mmol, 87.00% yield)

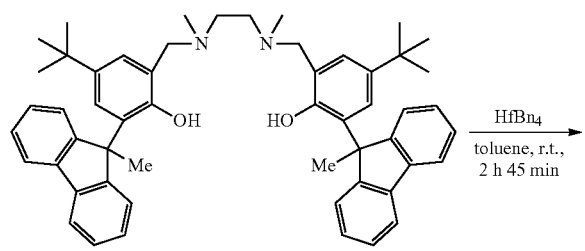

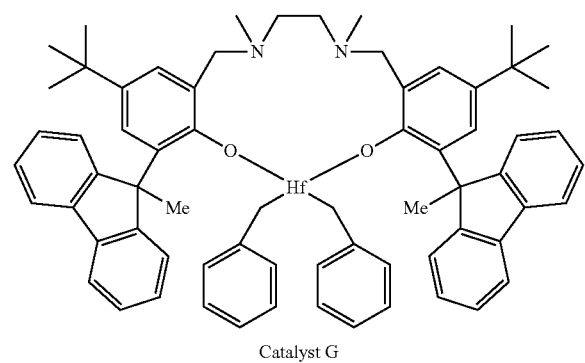

Catalyst G

In the dry-box, hafnium tetrabenzyl (11.8443 g, 21.812 mmol) is added as a solid to ligand G (16.7754 g, 21.813 mmol) in toluene (250 mL). This is stirred at room temperature for 2 h 45 min. Solvent is removed under a stream of nitrogen then placed under vacuum overnight, yielding a white solid (24.5863 g, 21.80 mmol, 99.95%).

Synthesis of Compound H

Compound H may be prepared by a procedure analogous to Compound G except that the step for preparing the methyl substituted fluorene precursor is modified to provide the 4-methyl phenyl substituted fluorene precursor.

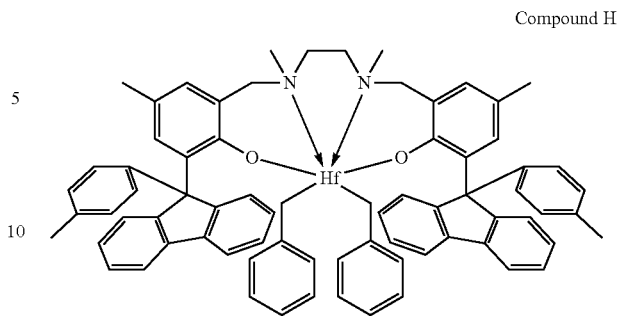

Compound H

Preparation of Supports

Silica Support (sMAO): Silica (D948, 40.7 g) is calcined at 600° C. then slurried in 200 mL of toluene. MAO (71.4 g of a 30 wt % toluene solution, 351.1 mmol of Al) is added slowly to the slurry. The slurry is then heated to 80° C. and stirred for 1 hr. The slurry is filtered, washed three times with 70 mL of toluene and once with pentane. The solid is dried under vacuum overnight to give a 60.7 g amount of free flowing white solid.

Fluorided Silica Support (F-sMAO): 1.18 g $(NH_4)_2SiF_6$ is dissolved in 7.00 g water in a 20 ml glass vial. 50 g silica (Grace D948) and 200 g of toluene are combined. Under vigorous stirring, the aqueous solution of $(NH_4)_2SiF_6$ is added via a syringe to the toluene slurry. The mixture is allowed to stir at room temperature for 2.5 h. The milky slurry is filtered through a 500 ml Optichem disposable polyethylene frit (40 micron), rinsed with 200 g pentane for three times, then dried in air overnight to yield a white, free-flowing solid. The solid is transferred into a tube furnace, and is heated to 200° C. under constant nitrogen flow (temperature program: 25° C./h ramped to 150° C.; held at 150° C. for 4 hours; 50° C./h ramped to 200° C.; held at 200° C. for 4 hours; cooled down to room temperature). 46 g of fluorided silica is collected after the calcination. Calculated F-loading: 0.8 mmol/g (F-loading =mmol of F/gram of added raw silica).

MAO (37.6 g of 30% wt in toluene) is added to a 250 ml celstir along with 100 mL of toluene. 29.9 g fluorided silica prepared in the previous step is added to the slurry in 5 g increments. The reaction stirred for 10 minutes at room temperature and is then heated to 100° C. for 3 hours. The solid is filtered, washed twice with 80 mL of toluene, washed twice with pentane, and dried under vacuum overnight. 39.6 g of free flowing white solid is collected.

Preparation of Supported Catalyst

Procedure I (Gram-scale Preparation of Supported Catalyst for HTPT Experiments)

21.3 mg Compound G (19 μmol) is dissolved in 1.0 g of toluene in a 20 ml glass vial. 0.986 g sMAO (3.2.1a) is slurried in 3.0 g of toluene in a 20 ml glass vial. The Compound G/toluene solution is added to the sMAO slurry via a pipette. The glass vial is capped with a Teflon-lined cap and vortexed at room temperature for 90 min. The resulting slurry is filtered through a 18 mL polyethylene frit (10 micron), and rinsed with 3 g toluene for 3 times, followed by 2 g of pentane for 3 times. The collected solid is dried under vacuum for 40 min. 0.968 g of supported OMC2144 is collected. Calculated catalyst loading: 19 μmol/g (catalyst loading=μmol of catalyst/gram of added sMAO).

Procedure II (Fluorided-sMAO)

32.2 mg catalyst Compound G (28 μmol) is combined with 0.71 g F-sMAO (3.2.1b) in a 20 ml glass vial. 4.0 g toluene solution is added to the glass vial. The glass vial is capped with a Teflon-lined cap and vortexed at room temperature for 90 min. The resulting slurry is filtered through a 18 mL polyethylene frit (10 micron), and rinsed with 3 g toluene for 3 times, followed by 2 g of pentane for 3 times. The collected solid is dried under vacuum for 40 min. 0.74 g of supported Compound G is collected. Calculated catalyst loading: 40 µmol/g (Catalyst loading=µmol of catalyst/gram of added sMAO).

Ethylene/1-hexene Copolymerization.

Preparation of catalyst slurry for high throughput run: In a dry box, 45 mg of supported catalyst is weighed into a 20 ml glass vial. 15 ml of toluene is added to the vial to make a slurry that contained 3 mg supported catalyst/ml slurry. The resulting mixture is vortexed prior to injection.

Starting material preparations: Solvents, polymerization grade toluene, and isohexane are supplied by ExxonMobil Chemical Company and thoroughly dried and degassed prior to use. Polymerization grade ethylene is used and further purified by passing it through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves purchased from Aldrich Chemical Company. TnOAl (tri-n-octylaluminum, neat) is used as a 2 mmol/L solution in toluene.

Reactor Description and Preparation

Polymerizations are conducted in an inert atmosphere (N2) drybox using autoclaves equipped with an external heater for temperature control, glass inserts (internal volume of reactor=22.5 mL), septum inlets, regulated supply of nitrogen, ethylene and hexene, and equipped with disposable PEEK mechanical stirrers (800 RPM). The autoclaves are prepared by purging with dry nitrogen prior to use.

Examples 1-10

Ethylene/1-hexene Copolymerization

The reactor is prepared as described above, and then purged with ethylene. Isohexane, 1-hexene, and TnOAl are added via syringe at room temperature and atmospheric pressure. The reactor is then brought to process temperature (85° C.) and charged with ethylene to process pressure (130 psig=896 kPa) while stirring at 800 RPM. The catalyst metal compound (100 µL of a 3 mg/mL toluene slurry, unless indicated otherwise) is added via syringe with the reactor at process conditions. TnOAl is used as 200 µL of a 20 mmol/L in isohexane solution. Amounts of reagents not specified above are given in Table 1. No other reagent is used. Ethylene is allowed to enter (through the use of computer controlled solenoid valves) the autoclaves during polymerization to maintain reactor gauge pressure (+/−2 psig). Reactor temperature is monitored and typically maintained within +/−1° C. Polymerizations are halted by addition of approximately 50 psi $O_2$/Ar (5 mol % O2) gas mixture to the autoclaves for approximately 30 seconds. The polymerizations are quenched after a predetermined cumulative amount of ethylene had been added or for a maximum of 45 minutes polymerization time. In addition to the quench time for each run, the reactors are cooled and vented. The polymer is isolated after the solvent is removed in-vacuo. Yields reported include total weight of polymer and residual catalyst. Catalyst activity is reported as kilograms of polymer per mmol transition metal compound per hour of reaction time (kg/mmol·hr).

TABLE 1

| Ex. | Catalyst | Support | Catalyst Loading (µmol/g) | Activity (kg/mol * h) | Mw/1000 (g/mol) | Mw/Mn | wt % hexene in polymer |
|---|---|---|---|---|---|---|---|
| 1 | Compound A | F-sMAO | 41 | 78023 | 10 | 2.1 | 20.3 |
| 2 | Compound B | F-sMAO | 40 | 45502 | 363 | 5.7 | 3.2 |
| 3 | Compound C | F-sMAO | 40 | 39119 | 646 | 2.6 | 3.4 |
| 4 | Compound D | F-sMAO | 40 | 19287 | 1649 | 2.1 | 3.9 |
| 5 | Compound E | F-sMAO | 40 | 56383 | 844 | 2.7 | 3.7 |
| 6 | Compound F | F-sMAO | 40 | 10029 | 2232 | 2.3 | 3.4 |
| 7 | Compound G | F-sMAO | 40 | 32131 | 1375 | 2.2 | 4.2 |
| 8 | Compound H | F-sMAO | 35 | 8922 | 1472 | 2.0 | 3.6 |
| C9‡ | Compound G | sMAO | 19 | 35426 | 1225 | 2.1 | 5.1 |
| C10‡ | Catalyst 1* | sMAO | 40 | 18193 | 461 | 2.0 | 2.4 |

Run condition: isohexane as solvent, 85° C., 130 psi ethylene pressure, 30 µl (6 mol % in feed) 1-hexene, no hydrogen added.
‡Comparative Examples As the data of Table 1 shows the catalyst compounds, catalyst systems, and polymerization processes disclosed herein can produce polymers having improved properties, such as high comonomer incorporation compared to conventional supported catalysts.

Examples 11-22

Effect of Hydrogen Concentration

The supported catalysts are evaluated by high throughput polymerizations in slurry ethylene/1-hexene polymerization tests to determine the effect of hydrogen pressure on molecular weight of resulting polyethylene polymer. For experiments with 0 ppm added hydrogen, ethylene gas is used as the feed. For experiments with 300 ppm added hydrogen, pre-mixed custom gas that contains 300 ppm $H_2$ in ethylene is used as feed. Results for these experiments are recorded in Table 2. These catalyst compositions show a wide range of responses to hydrogen concentration and are typically less sensitive to hydrogen concentration than conventional supported catalysts.

TABLE 2

| Ex. | Catalyst | Added $H_2$ (ppm) | Activity (kg/mol * h) | Mw/1000 (g/mol) | Mw/Mn | wt % hexene in polymer |
|---|---|---|---|---|---|---|
| 11 | Compound H | 0 | 8922 | 1472 | 2.0 | 3.6 |
| 12 | Compound H | 300 | 8921 | 566 | 2.0 | 2.9 |

TABLE 2-continued

| Ex. | Catalyst | Added H$_2$ (ppm) | Activity (kg/mol * h) | Mw/ 1000 (g/mol) | Mw/ Mn | wt % hexene in polymer |
|---|---|---|---|---|---|---|
| 13 | Compound G | 0 | 32131 | 1375 | 2.2 | 4.2 |
| 14 | Compound G | 300 | 31891 | 1004 | 2.2 | 4.8 |
| 15 | Compound C | 0 | 39119 | 646 | 2.6 | 3.4 |
| 16 | Compound C | 300 | 105032 | 374 | 2.2 | 3.4 |
| 17 | Compound D | 0 | 19287 | 1649 | 2.1 | 3.9 |
| 18 | Compound D | 300 | 19219 | 976 | 2.1 | 4.8 |
| 19 | Compound E | 0 | 56383 | 844 | 2.7 | 3.7 |
| 20 | Compound E | 300 | 69365 | 428 | 2.5 | 3.5 |
| 21 | Compound F | 0 | 10029 | 2232 | 2.3 | 3.4 |
| 22 | Compound F | 300 | 9109 | 646 | 2.5 | 3.6 |
| C23‡ | Catalyst 1 | 0 | 18193 | 461 | 2.0 | 2.4 |
| C24‡ | Catalyst 1 | 300 | 21706 | 260 | 1.8 | 2.6 |

Run condition: isohexane as solvent, 85° C., 130 psi ethylene pressure, 30 μl (6 mol % in feed) 1-hexene.
‡Comparative Examples Example 25

In Example 25, 48.8 g of F-sMAO (3.2.1b) is slurried in 180 mL of toluene. 2.20 g complex Compound G (1.95 mmol) is added as a solid to the slurry and washed down with 20 mL of toluene. The slurry is stirred for 1 hour and is then filtered and washed three times with 50 mL of toluene and twice with pentane. The solid is dried under vacuum overnight to give 50.0 grams of off-white powder.

Example 26

The polymerization with the supported catalyst form Example 25 is performed in a gas-phase fluidized bed reactor with a 6" body and a 10" expanded section. Cycle and feed gases are fed into the reactor body through a perforated distributor plate, and the reactor is controlled at 300 psi and 70 mol % ethylene. Reactor temperature is maintained by heating the cycle gas. Supported catalyst is fed as a 10 wt % slurry in Sono Jell® from Sonneborn (Parsippany, N.J.). The slurry is thinned and delivered to the reactor by nitrogen and isopentane feeds in the cat probe. Products are collected from the reactor, as necessary, to maintain the desired bed weight. Average process conditions are: Temperature: 85° C., Pressure: 300 psi, ethylene concentration: 70.0 mol %, hydrogen concentration: 949 ppm, hexene concentration: 0.30 mol %, bed wt.: 2000 g, Residence time: 4.6 hours, Cycle gas velocity: 1.48 ft/s, production rate: 436 g/hour, Activity: 1508 g(polymer)/g(supported catalyst), Catalyst Slurry Feed rate: 3.3 cc/hour, N$_2$ Catalyst Probe feed rate: 6000 cc/min; isopentane probe feed rate: 1 g/min.

The resulting polymer had a melt index, I$_2$, of 0.96 g/10 min., a high load melt index (I$_{21}$) of 23.84 g/10 min., a density of 0.9188 g/cm$^3$, a bulk density of 0.4854 g/cm$^3$.

Example 27

In a 4 L stainless steel batch reactor equipped with an overhead stir combined 1000 g MAO toluene solution (30 wt %) and 2000 g toluene. The mixture is stirred at 60 rpm for 5 min at room temperature. 803 g fluorided D948 silica (3.2.1b) is slowly added to the reactor. The resulting slurry is stirred at 120 rpm for 5 min at room temperature. The reactor is then sealed and heated to 100° C. for 3 hours. Once the reactor cooled to ambient temperature (below 35° C.), 39.5 g the fluoride silica supported Catalyst G (35.0 mmol) is added via an addition port to the reactor, and 100 g of rinse toluene is subsequently added through the addition port to ensure all solid catalyst is transferred into the reactor. The resulting mixture in the reactor is allowed to stir at room temperature at 120 rpm for 1 hour. The reactor is then placed under vacuum, and the solvent in the reactor is removed over 48 hours with constant stirring at 8 rpm. Lastly, the top of the reactor is opened and the supported catalyst is collected as a white, free-flowing solid (1146 gram).

Reaction is carried out in an 18" diameter fluidized bed gas phase reactor with a tapered expanded section with a maximum diameter of 50." The body of the reactor is 10 feet tall, and the expanded section is 8.5 feet tall. Product is removed from the reactor to maintain a constant bed fluidization level at the top of the reactor body. Catalyst is fed as a 20 wt % slurry in mineral oil. Conditions from the run are shown in Table 3.

TABLE 3

| Process Conditions | |
|---|---|
| H$_2$ conc. (mol ppm) | 949 |
| C$_6$/C$_2$ ratio (mol %/mol %) | 0.004 |
| Comonomer conc. (mol %) | 0.30 |
| C$_2$ conc. (mol %) | 70.0 |
| Reactor pressure (psig) | 300 |
| Reactor temp. (° C.) | 85 |
| Production rate (lb/hr) | 436 |
| Residence Time (hr) | 4.6 |
| Bed Weight (g) | 2000 |
| Cycle gas velocity (ft/sec.) | 1.48 |
| Catalyst Slurry feed (cc/hr) | 3.3 |
| Activity (g polymer/g catalyst) | 1508 |
| Polymer Properties | |
| Melt Index (I$_2$, g/10 min.) | 0.96 |
| HLMI (I$_{21}$, g/10 min.) | 23.84 |
| I$_{21}$/I$_2$ | 24.92 |
| Density (g/cm$^3$) | 0.9188 |
| Bulk Density (g/cm$^3$) | 0.4854 |

The catalysts in an embodiment provide improvement in catalyst activity, produce polymers with improved properties, or both. In an embodiment, crystallographic techniques indicate that the appended ring system or systems (e.g., the carbazole ring systems) are oriented transversely, e.g., perpendicular, to the phenol rings. In an embodiment, these catalysts have a structure to provide a broad corridor for the polymeryl moiety to reside and for the monomer to insert during the polymerization process. As such, catalysts according to one embodiment of the instant disclosure provide for an ability to control one or more characteristics of polymerization, tacticity, comonomer insertion, and the like.

All documents described herein are incorporated by reference herein, including any priority documents and/or testing procedures to the extent they are not inconsistent with this text As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements, and vice versa.

What is claimed is:

1. A catalyst system comprising the reaction product of a fluorided support, an activator, and a catalyst compound represented by Formula I:

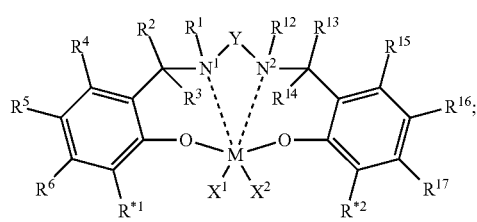

Formula I wherein:
each solid line represents a covalent bond and each dashed line represents a coordinative link;
wherein M is a Group 3, 4, 5, or 6 transition metal;
$N^1$ and $N^2$ are nitrogen;
O is oxygen;
each of $X^1$ and $X^2$ is, independently, or a univalent $C_1$ to $C_{20}$ hydrocarbyl radical, a univalent substituted $C_1$ to $C_{20}$ hydrocarbyl radical, or $X^1$ and $X^2$ join together to form a $C_4$ to $C_{62}$ cyclic or polycyclic ring structure, provided, that when M is trivalent $X^2$ is not present;
each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$ to $C_{40}$ hydrocarbyl radical, or a substituted $C_1$ to $C_{40}$ hydrocarbyl radical, optionally, two or more of $R^1$, $R^2$, $R^3$, $R^4$, $R^5$, $R^6$, $R^{12}$, $R^{13}$, $R^{14}$, $R^{15}$, $R^{16}$, and $R^{17}$ independently join together to form a $C_4$ to $C_{62}$ cyclic or polycyclic ring structure;
wherein $R^{*1}$ and $R^{*2}$ independently comprise a bulky functional group, an electron withdrawing group, or a combination thereof; and
Y is a divalent $C_1$ to $C_{20}$ hydrocarbylene radical.

2. The catalyst system of claim 1, wherein the fluorided support comprises fluorided silica.

3. The catalyst system of claim 2, wherein the fluorided silica has not been calcined at a temperature of 400° C. or more.

4. The catalyst system of claim 3, wherein $X^1$ and $X^2$ are benzyl radicals and Y is selected from the group consisting of —CH$_2$CH$_2$—, 1,2-cyclohexylene, and —CH$_2$CH$_2$CH$_2$—.

5. The catalyst system of claim 1, wherein $X^1$ and $X^2$ are benzyl radicals and Y is selected from the group consisting of —CH$_2$CH$_2$—, 1,2-cyclohexylene, and —CH$_2$CH$_2$CH$_2$—.

6. The catalyst system of claim 1, wherein $R^{*1}$ and $R^{*2}$ each comprises a cyclopentadienyl radical represented by Formula II:

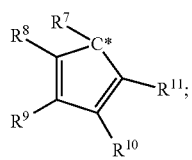

Formula II wherein:
C* indicates an attachment carbon of the radical;
$R^7$ is a $C_1$ to $C_{40}$ hydrocarbyl radical or a substituted $C_1$ to $C_{40}$ hydrocarbyl radical; and
each of $R^8$, $R^9$, $R^{10}$, and $R^{11}$ is, independently, a hydrogen, a $C_1$ to $C_{40}$ hydrocarbyl radical, or a substituted $C_1$ to $C_{40}$ hydrocarbyl radical, optionally, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure.

7. The catalyst system of claim 1, wherein the catalyst compound is represented by Formula III:

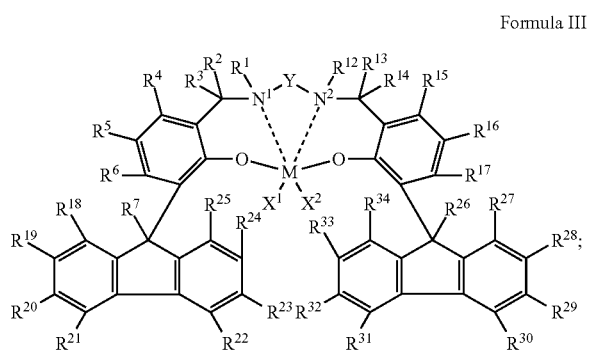

Formula III wherein:
each of $R^7$ and $R^{26}$ is, independently, a $C_1$-$C_{40}$ hydrocarbyl radical or a substituted $C_1$ to $C_{40}$ hydrocarbyl radical;
wherein each of $R^{18}$, $R^{19}$, $R^{20}$, $R^{21}$, $R^{22}$, $R^{23}$, $R^{24}$, $R^{25}$, $R^{27}$, $R^{28}$, $R^{29}$, $R^{30}$, $R^{31}$, $R^{32}$, $R^{33}$, and $R^{34}$ is, independently, hydrogen, a $C_1$ to $C_{40}$ hydrocarbyl radical, or a substituted $C_1$ to $C_{40}$ hydrocarbyl radical,
M is a Group 3, 4, 5, or 6 transition metal;
Y is a divalent $C_1$ to $C_{20}$ hydrocarbylene radical;
$N^1$ and $N^2$ are nitrogen;
O is oxygen;
each of $X^1$ and $X^2$ is, independently, or a univalent $C_1$ to $C_{20}$ hydrocarbyl radical, a univalent substituted $C_1$ to $C_{20}$ hydrocarbyl radical, or $X^1$ and $X^2$ join together to form a $C_4$ to $C_{62}$ cyclic or polycyclic ring structure, provided that when M is trivalent $X^2$ is not present;
each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$ to $C_{40}$ hydrocarbyl radical, or a substituted $C_1$ to $C_{40}$ hydrocarbyl radical; and
wherein two or more of $R^1$, $R^2$, $R^3$, $R^4$, $R^5$, $R^6$, $R^7$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, and $R^{25}$ may independently join together to form a $C_4$ to $C_{62}$ cyclic or polycyclic ring structure, or.

8. The catalyst system of claim 7, wherein $X^1$ and $X^2$ are benzyl radicals and Y is selected from the group consisting of —CH$_2$CH$_2$—, 1,2-cyclohexylene, and —CH$_2$CH$_2$CH$_2$—.

9. The catalyst system of claim 2, wherein R*¹ and R*² each comprise a pyrrole radical is represented by Formula IV:

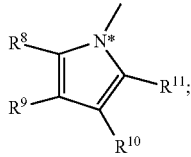

Formula IV wherein:
N* indicates an attachment nitrogen of the radical;
each of $R^8$, $R^9$, $R^{10}$, and $R^{11}$ is, independently, a hydrogen, a $C_1$ to $C_{40}$ hydrocarbyl radical, or a functional group comprising elements from Groups 13 to 17 of the periodic table of the elements, optionally, two or more of $R^1$, $R^2$, $R^3$, $R^4$, $R^5$, $R^6$, $R^8$, $R^9$, $R^{10}$, $R^{11}$, $R^{12}$, $R^{13}$, $R^{14}$, $R^{15}$, $R^{16}$, and $R^{17}$ independently join together to form a $C_4$ to $C_{62}$ cyclic or polycyclic ring structure.

10. The catalyst system of claim 1, wherein the catalyst compound is represented by Formula V:

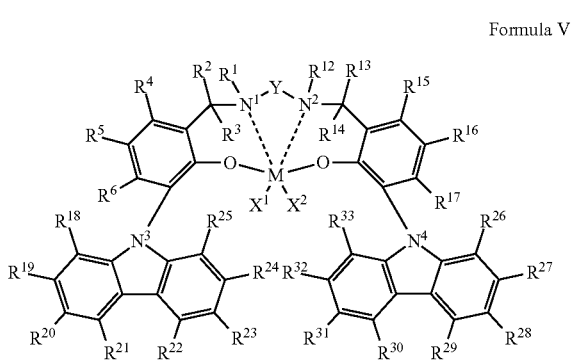

Formula V wherein:
each of $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ is, independently, a hydrogen, a $C_1$ to $C_{40}$ hydrocarbyl radical, or a substituted $C_1$ to $C_{40}$ hydrocarbyl radical, optionally two or more of $R^1$ to $R^6$ and $R^{12}$ to $R^{33}$ may independently join together to form a $C_4$ to $C_{62}$ cyclic or polycyclic ring structure;
M is a Group 3, 4, 5, or 6 transition metal;
Y is a divalent $C_1$ to $C_{20}$ hydrocarbylene radical;
$N^1$, $N^2$, $N^3$, and $N^4$ are nitrogen;
O is oxygen;
each of $X^1$ and $X^2$ is, independently, or a univalent $C_1$ to $C_{20}$ hydrocarbyl radical, a or univalent substituted $C_1$ to $C_{20}$ hydrocarbyl radical, or $X^1$ and $X^2$ join together to form a $C_4$ to $C_{62}$ cyclic or polycyclic ring structure, provided that when M is trivalent $X^2$ is not present; and
each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$ to $C_{40}$ hydrocarbyl radical, or a substituted $C_1$ to $C_{40}$ hydrocarbyl radical.

11. The catalyst system of claim 10, wherein $X^1$ and $X^2$ are benzyl radicals and Y is selected from the group consisting of —CH₂CH₂—, 1,2-cyclohexylene, and —CH₂CH₂CH₂—.

12. The catalyst system of claim 1, wherein the catalyst compound is represented by Formula VI:

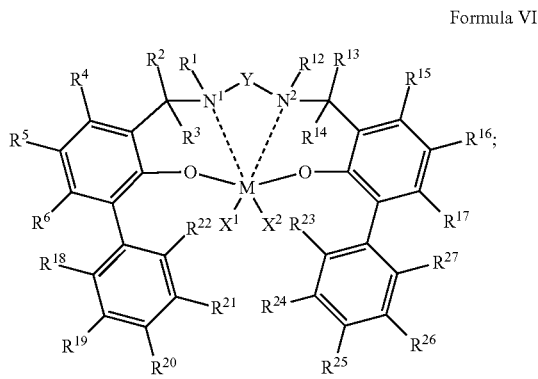

Formula VI wherein:
each of $R^{18}$, $R^{19}$, $R^{20}$, $R^{21}$, $R^{22}$, $R^{23}$, $R^{24}$, $R^{25}$, $R^{26}$, and $R^{27}$ is, independently, a hydrogen, a $C_1$ to $C_{40}$ hydrocarbyl radical, or a substituted $C_1$ to $C_{40}$ hydrocarbyl radical, optionally two or more of $R^1$ to $R^6$ and $R^{12}$ to $R^{27}$ may independently join together to form a $C_4$ to $C_{62}$ cyclic or polycyclic ring structure, or a combination thereof;
M is a Group 3, 4, 5, or 6 transition metal;
Y is a divalent $C_1$ to $C_{20}$ hydrocarbylene radical;
$N^1$ and $N^2$ are nitrogen;
O is oxygen;
each of $X^1$ and $X^2$ is, independently, or a univalent $C_1$ to $C_{20}$ hydrocarbyl radical, a univalent substituted $C_1$ to $C_{20}$ hydrocarbyl radical, or $X^1$ and $X^2$ join together to form a $C_4$ to $C_{62}$ cyclic or polycyclic ring structure, provided that when M is trivalent $X^2$ is not present; and
each $R^1$, $R^2$, $R^3$, $R^4$, $R^5$, $R^6$, $R^{12}$, $R^{13}$, $R^{14}$, $R^{15}$, $R^{16}$, and $R^{17}$ is, independently, hydrogen, a $C_1$ to $C_{40}$ hydrocarbyl radical, or a substituted $C_1$ to $C_{40}$ hydrocarbyl radical.

13. The catalyst system of claim 12, wherein $X^1$ and $X^2$ are benzyl radicals and Y is selected from the group consisting of —CH₂CH₂—, 1,2-cyclohexylene, and —CH₂CH₂CH₂—.

14. The catalyst system of claim 1, wherein the catalyst compound has a structure according to Formula VII:

Formula VII

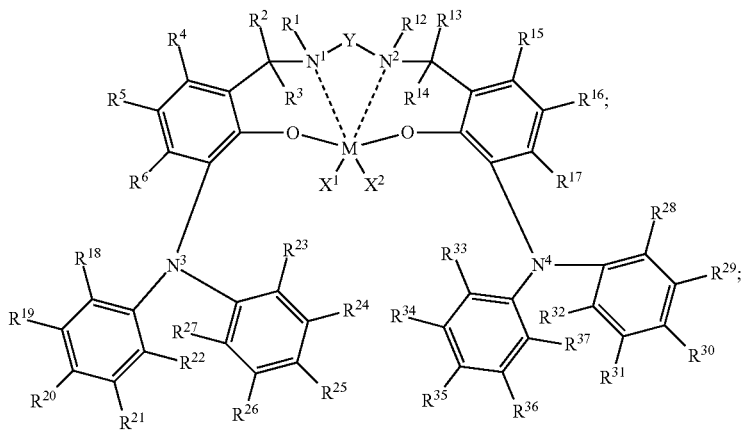

wherein:

M is a Group 3, 4, 5, or 6 transition metal;

$N^1$, $N^2$, $N^3$, and $N^4$ are nitrogen;

O is oxygen;

each of $X^1$ and $X^2$ is, independently, or a univalent $C_1$ to $C_{20}$ hydrocarbyl radical, a univalent substituted $C_1$ to $C_{20}$ hydrocarbyl radical, or $X^1$ and $X^2$ join together to form a $C_4$ to $C_{62}$ cyclic or polycyclic ring structure, provided however when M is trivalent $X^2$ is not present;

Y is a divalent hydrocarbylene radical covalently bonded to and bridging between both of the nitrogen atoms $N^1$ and $N^2$; and each of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$, and is, independently, a hydrogen, a $C_1$ to $C_{40}$ hydrocarbyl radical, or a substituted $C_1$ to $C_{40}$ hydrocarbyl radical, optionally two or more of $R^1$, $R^2$, $R^3$, $R^4$, $R^5$, $R^6$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, and $R^{37}$ may independently join together to form a $C_4$ to $C_{62}$ cyclic or polycyclic ring structure wherein neither $R^{18}$ and nor $R^{22}$ join together with $R^{23}$ or $R^{27}$ to form direct covalent bonds between the respective aromatic rings and wherein neither $R^{33}$ and nor $R^{37}$ join together with $R^{28}$ or $R^{32}$ to form direct covalent bonds between the respective aromatic rings.

15. The catalyst system of claim 14, wherein $X^1$ and $X^2$ are benzyl radicals and Y is selected from the group consisting of —$CH_2CH_2$—, 1,2-cyclohexylene, and —$CH_2CH_2CH_2$—.

16. The catalyst system of claim 14, wherein the fluorided support comprises fluorided silica.

17. The catalyst system of claim 16, wherein the fluorided silica has not been calcined at a temperature of 400° C. or more.

18. The catalyst system of claim 1, wherein the catalyst compounds are represented by Formula VIII:

Formula VIII

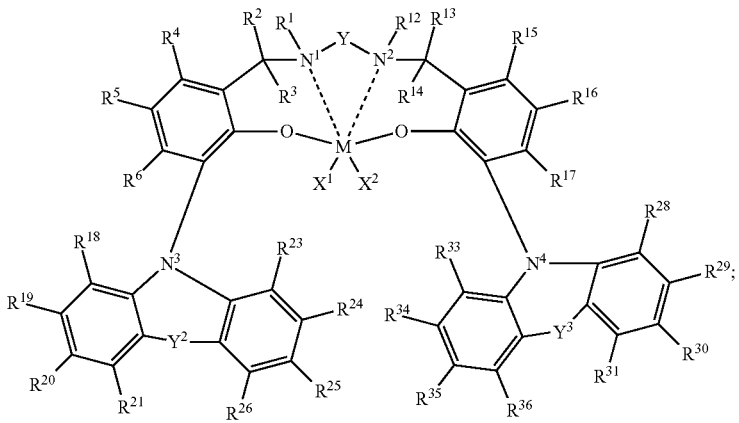

wherein;

M is a Group 3, 4, 5, or 6 transition metal;

$N^1$, $N^2$, $N^3$, and $N^4$ are nitrogen;

O is oxygen;

each of $X^1$ and $X^2$ is, independently, a univalent $C_1$ to $C_{20}$ hydrocarbyl radical, or a substituted $C_1$ to $C_{20}$ hydrocarbyl radical, or $X^1$ and $X^2$ join together to form a $C_4$ to $C_{62}$ cyclic or polycyclic ring structure, provided that when M is trivalent $X^2$ is not present;

Y is or a divalent $C_1$ to $C_{20}$ hydrocarbylene radical;

$Y^2$ and $Y^3$ are independently a divalent $C_1$ to $C_{20}$ hydrocarbylene radical, a divalent functional group comprising elements from Groups 13 to 16 of the periodic table of the elements; and each $R^1$ to $R^6$, $R^{12}$ to $R^{21}$, $R^{23}$ to $R^{26}$, $R^{28}$ to $R^{31}$, and $R^{33}$ to $R^{36}$ is, independently, a hydrogen, a $C_1$ to $C_{40}$ hydrocarbyl radical, or a substituted $C_1$ to $C_{40}$ hydrocarbyl radical, optionally two or more of $R^1$ to $R^6$, $R^{12}$ to $R^{21}$, $R^{23}$ to $R^{26}$, $R^{28}$ to $R^{31}$, and $R^{33}$ to $R^{36}$ may independently join together to form a $C_4$ to $C_{62}$ cyclic or polycyclic ring structure.

19. The catalyst system of claim 14, wherein $X^1$ and $X^2$ are benzyl radicals and Y is selected from the group consisting of —$CH_2CH_2$—, 1,2-cyclohexylene, and —$CH_2CH_2CH_2$—.

20. A polymerization process to produce polyolefin comprising:
 a) contacting one or more olefin monomers with the catalyst system of claim 1, and
 b) obtaining olefin polymer.

21. The process of claim 20, wherein the activator is an alumoxane.

22. The process of claim 20, wherein the activator is not a non-coordinating anion.

23. The process of claim 20, wherein contacting one or more olefin monomers with the catalyst system includes contacting one or more olefin monomers with a chain transfer agent.

24. The process of claim 23, wherein the chain transfer agent is represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

25. A polymerization process to produce polyolefin comprising:
 a) contacting one or more olefin monomers with the catalyst system of claim 2, and
 b) obtaining olefin polymer.

26. The process of claim 25, wherein the activator is an alumoxane.

27. The process of claim 25, wherein the activator is not a non-coordinating anion.

28. The process of claim 25, wherein contacting one or more olefin monomers with the catalyst system includes contacting one or more olefin monomers with a chain transfer agent represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

29. A polymerization process to produce polyolefin comprising:
 a) contacting one or more olefin monomers with the catalyst system of claim 2, and
 b) obtaining olefin polymer.

30. The process of claim 29, wherein the activator is an alumoxane.

31. The process of claim 29, wherein the activator is not a non-coordinating anion.

32. The process of claim 29, wherein contacting one or more olefin monomers with the catalyst system includes contacting one or more olefin monomers with a chain transfer agent represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

33. A polymerization process to produce polyolefin comprising:
 a) contacting one or more olefin monomers with the catalyst system of claim 4, and
 b) obtaining olefin polymer.

34. The process of claim 33, wherein the activator is an alumoxane.

35. The process of claim 33, wherein the activator is not a non-coordinating anion.

36. The process of claim 33, wherein contacting one or more olefin monomers with the catalyst system includes contacting one or more olefin monomers with a chain transfer agent represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

37. A polymerization process to produce polyolefin comprising: a) contacting one or more olefin monomers with the catalyst system of claim 7, and b) obtaining olefin polymer.

38. The process of claim 37, wherein the activator is an alumoxane.

39. The process of claim 37, wherein the activator is not a non-coordinating anion.

40. The process of claim 37, wherein contacting one or more olefin monomers with the catalyst system includes contacting one or more olefin monomers with a chain transfer agent represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

41. A polymerization process to produce polyolefin comprising:
 a) contacting one or more olefin monomers with the catalyst system of claim 10, and
 b) obtaining olefin polymer.

42. The process of claim 41, wherein the activator is an alumoxane.

43. The process of claim 41, wherein the activator is not a non-coordinating anion.

44. The process of claim 41, wherein contacting one or more olefin monomers with the catalyst system includes contacting one or more olefin monomers with a chain transfer agent represented by the formula $R_3Al$, $R_2Zn$, or $R_2Zn$ and $R_3Al$, and is present at a molar ratio of transition metal to Al, Zn, or Al and Zn, respectively, of at least 10:1, where R is a $C_1$ to $C_{40}$ alkyl group.

45. A polymerization process to produce polyolefin comprising:
 a) contacting one or more olefin monomers with the catalyst system of claim 12, and
 b) obtaining olefin polymer.

46. A polymerization process to produce polyolefin comprising:
 a) contacting one or more olefin monomers with the catalyst system of claim 14, and
 b) obtaining olefin polymer.

47. A polymerization process to produce polyolefin comprising:
 a) contacting one or more olefin monomers with the catalyst system of claim 18, and
 b) obtaining olefin polymer.

* * * * *